United States Patent
Chow et al.

(10) Patent No.: US 11,167,080 B2
(45) Date of Patent: *Nov. 9, 2021

(54) BALLOON DILATION CATHETER SYSTEM FOR TREATMENT AND IRRIGATION OF THE SINUSES

(71) Applicant: Acclarent, Inc., Irvine, CA (US)

(72) Inventors: Mina W. Chow, Campbell, CA (US); Thomas R. Jenkins, Alameda, CA (US); Arthur M. Lin, Fremont, CA (US); Mei Y. Pader, Fremont, CA (US); Jessica K. Chan, Sunnyvale, CA (US); Scott O. Chamness, Menlo Park, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/224,345

(22) Filed: Apr. 7, 2021

(65) Prior Publication Data

US 2021/0220546 A1 Jul. 22, 2021

Related U.S. Application Data

(60) Continuation of application No. 17/121,864, filed on Dec. 15, 2020, which is a continuation of application
(Continued)

(51) Int. Cl.
*A61M 3/02* (2006.01)
*A61M 25/10* (2013.01)
(Continued)

(52) U.S. Cl.
CPC .............. *A61M 3/0295* (2013.01); *A61B 1/06* (2013.01); *A61B 17/24* (2013.01); *A61M 3/0258* (2013.01);
(Continued)

(58) Field of Classification Search
CPC ........ A61M 25/0113; A61M 25/09041; A61M 2025/09116; A61M 2025/0037;
(Continued)

(56) References Cited

U.S. PATENT DOCUMENTS

| 6,217,547 B1 | 4/2001 | Lee |
| 7,645,272 B2 | 1/2010 | Chang et al. |

(Continued)

FOREIGN PATENT DOCUMENTS

| CN | 102159276 A | 8/2011 |
| JP | 2002-512534 A | 4/2002 |

(Continued)

OTHER PUBLICATIONS

U.S. Appl. No. 17/121,864.
(Continued)

*Primary Examiner* — Nathan R Price
*Assistant Examiner* — Justin L Zamory
(74) *Attorney, Agent, or Firm* — Frost Brown Todd LLC

(57) ABSTRACT

A medical device for the treatment and irrigation of a sinus opening is described. The device allows for single-handed operation to access, dilate and irrigate a sinus opening. The device includes a sinus guide catheter, a guiding element, a balloon dilation catheter, a balloon catheter movement mechanism and a guiding element movement mechanism. A method for treating a sinus opening and irrigating a sinus is also described.

1 Claim, 18 Drawing Sheets

Related U.S. Application Data

No. 15/415,746, filed on Jan. 25, 2017, now Pat. No. 10,905,820, which is a division of application No. 13/827,593, filed on Mar. 14, 2013, now Pat. No. 9,579,448.

(60) Provisional application No. 61/698,040, filed on Sep. 7, 2012, provisional application No. 61/675,569, filed on Jul. 25, 2012, provisional application No. 61/623,892, filed on Apr. 13, 2012.

(51) Int. Cl.
*A61M 25/09* (2006.01)
*A61B 1/06* (2006.01)
*A61B 17/24* (2006.01)
*A61M 25/01* (2006.01)
*A61M 29/02* (2006.01)
*A61M 25/00* (2006.01)

(52) U.S. Cl.
CPC .... *A61M 25/0108* (2013.01); *A61M 25/0113* (2013.01); *A61M 25/09* (2013.01); *A61M 25/09041* (2013.01); *A61M 25/1002* (2013.01); *A61M 25/1018* (2013.01); *A61M 29/02* (2013.01); *A61B 2017/246* (2013.01); *A61M 2025/0008* (2013.01); *A61M 2025/1079* (2013.01); *A61M 2025/1093* (2013.01); *A61M 2210/0681* (2013.01)

(58) Field of Classification Search
CPC ........... A61M 2025/1093; A61M 2025/09008; A16M 3/0295; A61B 17/24; A61B 2017/246

See application file for complete search history.

(56) References Cited

U.S. PATENT DOCUMENTS

| | | | |
|---|---|---|---|
| 7,654,997 B2 | 2/2010 | Makower et al. | |
| 7,803,150 B2 | 9/2010 | Chang et al. | |
| 8,894,614 B2 | 11/2014 | Muni et al. | |
| 9,011,412 B2 | 4/2015 | Albritton, IV et al. | |
| 9,095,646 B2 | 8/2015 | Chow et al. | |
| 9,579,448 B2 * | 2/2017 | Chow | A61M 25/1018 |
| 10,905,820 B2 | 2/2021 | Chow et al. | |
| 2006/0004323 A1 | 1/2006 | Chang et al. | |
| 2007/0073269 A1 | 3/2007 | Becker | |
| 2010/0099946 A1 | 4/2010 | Jenkins et al. | |
| 2010/0274188 A1 | 10/2010 | Chang et al. | |
| 2012/0071856 A1 | 3/2012 | Goldfarb et al. | |
| 2012/0071857 A1 | 3/2012 | Goldfarb et al. | |

FOREIGN PATENT DOCUMENTS

| | | |
|---|---|---|
| JP | 2008-513125 A | 5/2008 |
| JP | 2010-220883 A | 10/2010 |
| JP | 2012-502749 A | 2/2012 |
| WO | WO 2011/140535 A1 | 11/2011 |
| WO | WO 2012/039905 A1 | 9/2012 |
| WO | WO 2013/016056 A2 | 1/2013 |

OTHER PUBLICATIONS

Chinese Search Report dated Apr. 18, 2016 for Application No. 201380019695.1, 2 pages.
Chinese Office Action dated May 5, 2016 for Application No. 201380019695.1. 12 pages.
Chinese Office Action dated Dec. 16, 2016 for Application No. 201680019695.1, 9 pages.
Chinese Office Action dated Aug. 3, 2017 for Application No. 201380019695.1, 9 pages.
European Communication dated Aug. 23, 2017 for Application No. 13718974.2, 3 pages.
International Search Report and Written Opinion dated Jul. 23, 2013 for International Application No. PCT/US2013/036362, 17 pages.
Japanese Notification of Reasons for Refusal dated Feb. 24, 2017 for Application No. 2015-505941, 5 pages.
Japanese Decision of Refusal dated Oct. 5, 2017 for Application No. 2015-505941, 4 pages.
Japanese Notification of Reasons for Refusal dated Mar. 5, 2019 for Application No. 2015-505941, 3 pages.
Japanese Notification of Reasons for Refusal dated Dec. 25, 2018 for Application No. 2018-025882, 3 pages.
Korean Office Action dated Jul. 29, 2019 for Application No. 10-2014-7031617, 2 pages.
U.S. Appl. No. 17/121,864, entitled "Balloon Dilation Catheter System for Treatment and Irrigation of the Sinuses," filed Dec. 15, 2020.

* cited by examiner

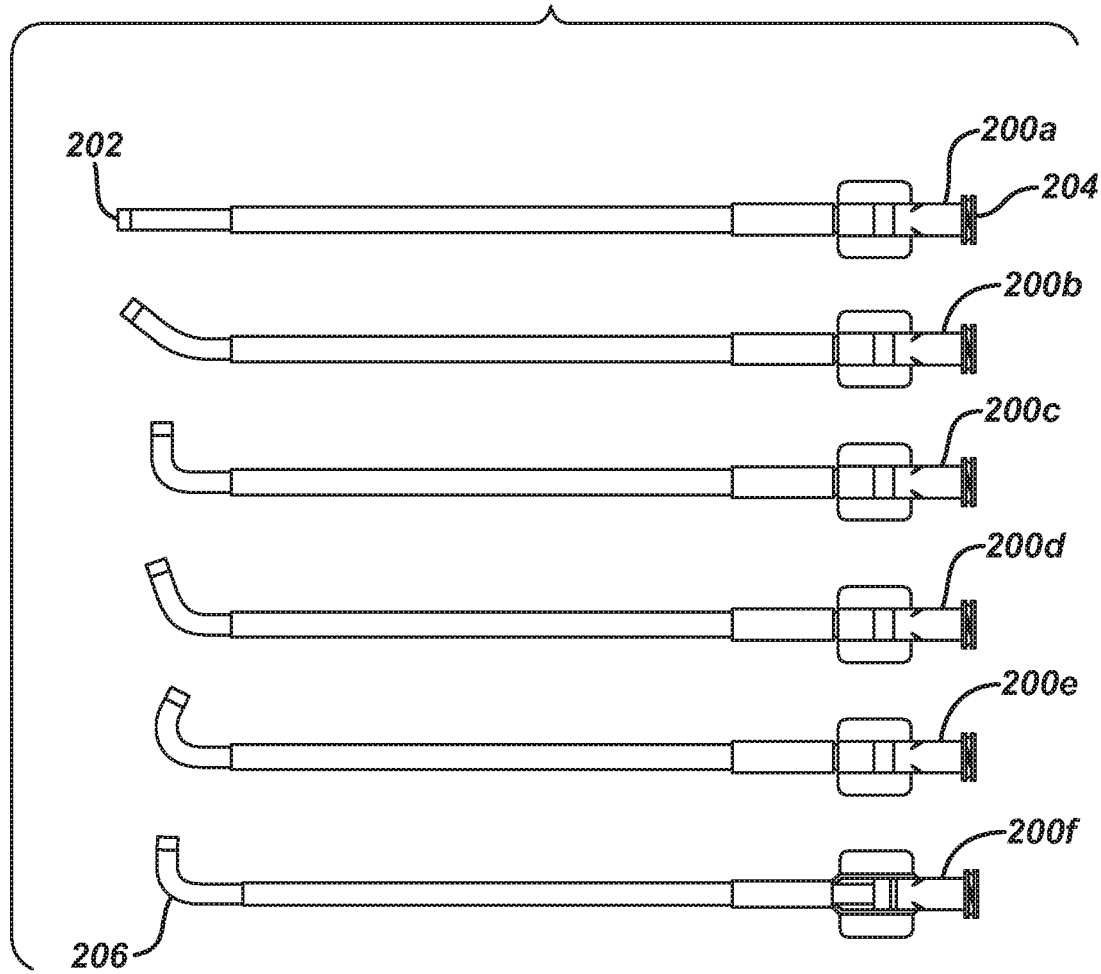

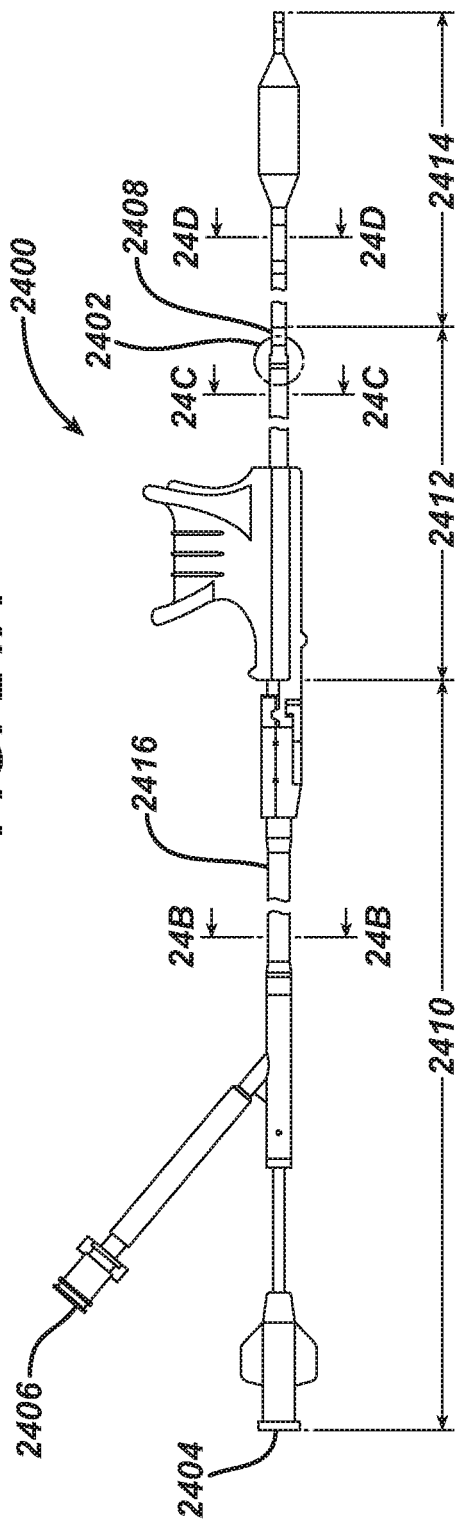
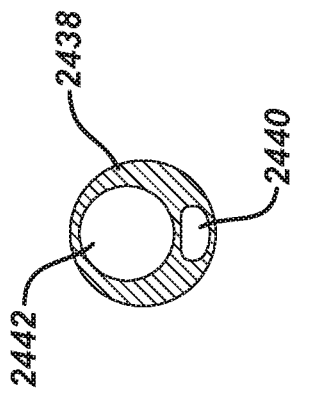
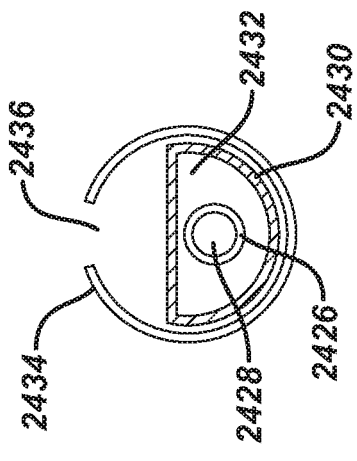
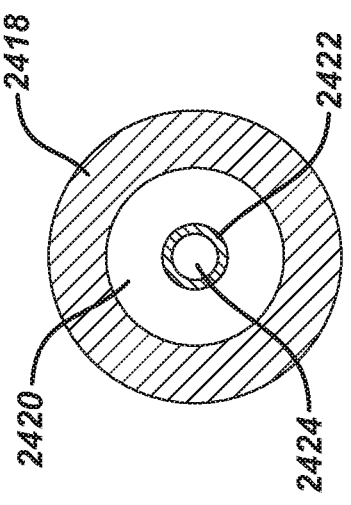

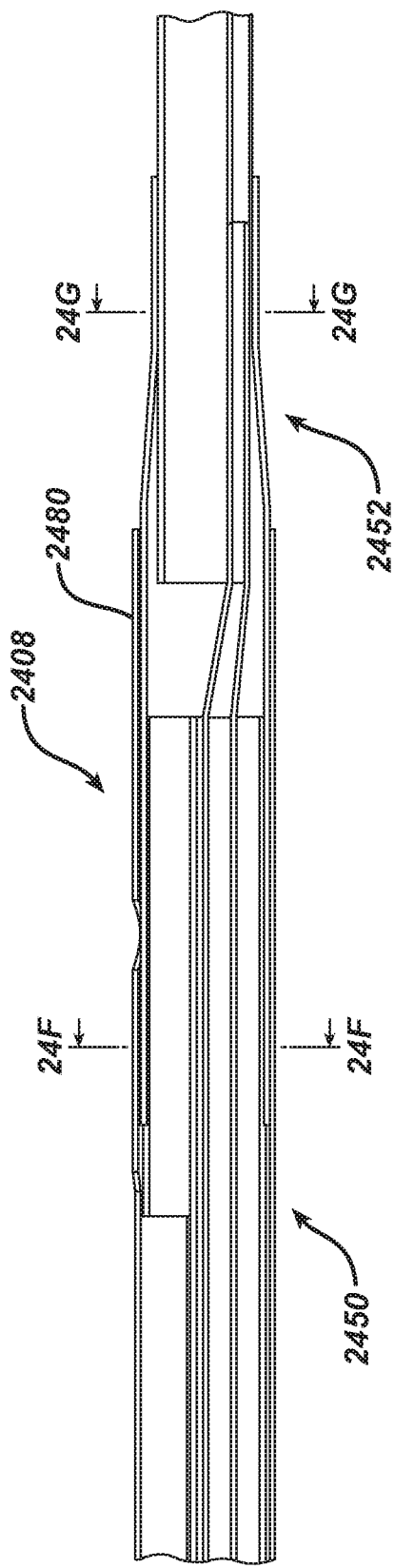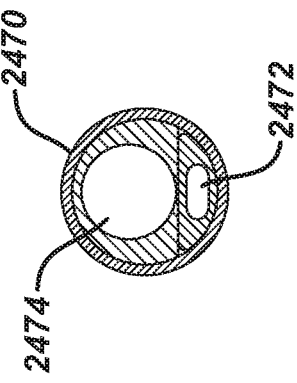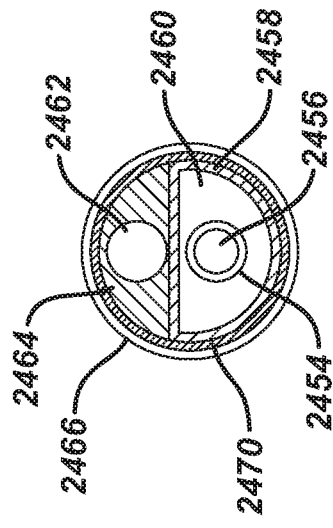

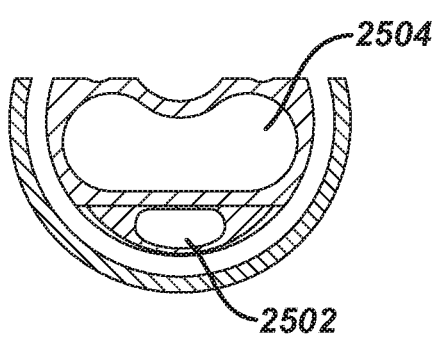
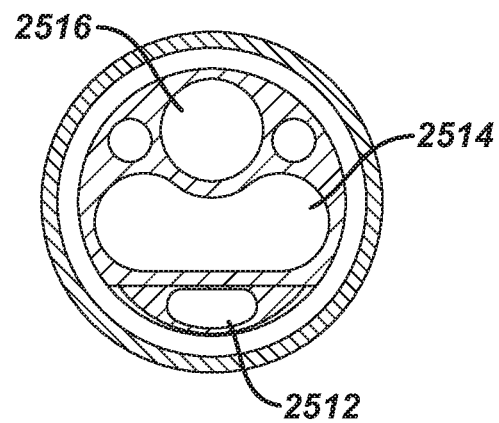
FIG. 25A
FIG. 25B

BALLOON DILATION CATHETER SYSTEM FOR TREATMENT AND IRRIGATION OF THE SINUSES

RELATED APPLICATIONS

This Application is a continuation of U.S. patent application Ser. No. 17/121,864 filed on Dec. 15, 2020, which is a continuation of U.S. patent application Ser. No. 15/415,746 filed on Jan. 25, 2017 (issued as U.S. Pat. No. 10,905,820 on Feb. 2, 2021), which is a divisional of U.S. patent application Ser. No. 13/827,593 filed on Mar. 14, 2013 (issued as U.S. Pat. No. 9,579,448 on Feb. 28, 2017), which claims priority pursuant to U.S.C. § 119 to U.S. Provisional Patent Application Ser. No. 61/623,892 entitled "Balloon Dilation Catheter for Treatment of the Sinuses" filed on Apr. 13, 2012, U.S. Provisional Patent Application Ser. No. 61/675,569 entitled "Balloon Dilation Catheter System for Treatment and Irrigation of the Sinuses" filed on Jul. 25, 2012, and U.S. Provisional Patent Application Ser. No. 61/698,040 entitled "Balloon Dilation Catheter System for Treatment and Irrigation of the sinuses" filed on Sep. 7, 2012, the entirety of these applications being incorporated herein by reference thereto.

FIELD OF THE INVENTION

The present invention relates, in general, to medical devices and, in particular, to medical devices and related methods for the treatment of sinus conditions.

BACKGROUND OF THE INVENTION

The paranasal sinuses are hollow cavities in the skull connected by small openings, known as ostia, to the nasal canal. Each ostium between a paranasal sinus and the nasal cavity is formed by a bone covered by a layer of mucosal tissue. Normally, air passes into and out of the paranasal sinuses through the ostia. Also, mucus is continually formed by the mucosal lining of the sinuses and drains through the ostia and into the nasal canal.

Sinusitis is a general term that refers to inflammation in one or more of the paranasal sinuses. Acute sinusitis can be associated with upper respiratory infections or allergic conditions, which may cause tissue swelling and temporarily impede normal trans-ostial drainage and ventilation of the sinuses, thereby resulting in some collection of mucus and possibly infection within the sinus cavities. Chronic sinusitis is a long term condition characterized by persistent narrowing or blockage of one or more sinus ostia, resulting in chronic infection and inflammation of the sinuses. Chronic sinusitis is often associated with longstanding respiratory allergies, nasal polyps, hypertrophic nasal turbinates and/or deviated internasal septum. While acute sinusitis is typically caused by infection with a single pathogen (e.g., one type of bacteria, one type of virus, one type of fungus, etc.), chronic sinusitis is often associated with multiple pathogen infections (e.g., more than one type of bacteria or more than one genus of micro-organism).

Chronic sinusitis, if left untreated, can result in irreparable damage to the tissues and/or bony structures of the paranasal anatomy. The initial treatment of chronic sinusitis usually involves the use of drugs such as decongestants, steroid nasal sprays and antibiotics (if the infection is bacterial). In cases where drug treatment alone fails to provide permanent relief, surgical intervention may be indicated.

The most common surgical procedure for treating chronic sinusitis is functional endoscopic sinus surgery (FESS). FESS is commonly performed using an endoscope and various rigid instruments inserted through the patient's nostril. The endoscope is used to visualize the positioning and use of various rigid instruments used for removing tissue from the nasal cavity and sinus ostia in an attempt to improve sinus drainage.

A technique known as the Balloon Sinuplasty™ procedure and a system for performing the procedure has been developed by Acclarent Inc, of Menlo Park, Calif. for the treatment of sinusitis. A number of U.S. patents and patent applications including U.S. Pat. Nos. 7,645,272, 7,654,997, and 7,803,150 describe various embodiments of the Balloon Sinuplasty™ procedure as well as various devices useable in the performance of such procedure. In the Balloon Sinuplasty™ procedure, a guide catheter is inserted into the nose and positioned within or adjacent to the ostium of the affected paranasal sinus. A guidewire is then advanced through the guide catheter and into the affected paranasal sinus. Thereafter, a dilation catheter having an expandable dilator (e.g. an inflatable balloon) is advanced over the guidewire to a position where the dilator is positioned within the ostium of the affected paranasal sinus. The dilator is then expanded, causing dilation of the ostium and remodelling of bone adjacent to the ostium, without required incision of the mucosa or removal of any bone. The catheters and guidewire are then removed and the dilated ostium allows for improved drainage from and ventilation of the affected paranasal sinus.

There is a continuing need for improved methods and devices for treating the paranasal sinus. Although the dilation catheter described above is easy to use, it would be useful to provide for a dilation catheter that could further irrigate the sinus such as that described in U.S. application Ser. No. 13/550,293 entitled Devices And Methods For Transnasal Dilation And Irrigation Of The Sinuses, issued as U.S. Pat. No. 9,095,646 on Aug. 4, 2015, which is hereby incorporated by reference in its entirety, when using the single-handed operable Balloon Sinuplasty™ system described in described in US Patent Publication No. 2012/0071856, issued as U.S. Pat. No. 9,554,817 on Jan. 31, 2017, which is hereby incorporated by reference in its entirety.

SUMMARY OF THE INVENTION

Accordingly, in one aspect, the invention is directed to a medical device for accessing, dilating and irrigating a sinus. The device includes a handle useful for single-handed operation of the medical device. The handle has a proximal end, a distal end and a handle body between the proximal end and the distal end. The device further includes a sinus guide catheter attached to the handle distal end. The device further includes a guiding element for accessing the sinus and a balloon dilation catheter for dilating and irrigating the sinus. A balloon catheter movement mechanism and a guiding element movement mechanism are slidable along the handle body for single handed movement of the guiding element and balloon catheter to access, dilate and irrigate the sinus without removing the medical device from the sinus.

In another embodiment of the medical device of the invention, the balloon catheter movement mechanism is configured for advancement or retraction of the balloon catheter through the handle and guide catheter using a single finger or thumb. In another embodiment, the guiding element movement mechanism is configured for advancement or retraction of the guiding element through the handle and guide catheter using a single finger or thumb. In yet another embodiment, the guiding element movement mechanism is further configured for rotation of the guiding element.

In a further embodiment of the medical device of the invention, the guiding element movement mechanism and the balloon catheter movement mechanism are located side by side. In another embodiment, the guiding element movement mechanism and the balloon catheter movement mechanism are located one on top of the other.

In another embodiment of the invention, the balloon dilation catheter comprises an integrated shaft system. In yet another embodiment, the integrated shaft system has a proximal portion and a distal portion and the integrated shaft system has an inflation lumen that extends through the proximal portion and the distal portion, a combined irrigation lumen and guiding element lumen in the distal portion, and coaxial irrigation and guiding element lumens in the proximal portion. In still another embodiment, the integrated shaft system has a proximal portion and a distal portion and the integrated shaft system has an inflation lumen that extends through the proximal portion and the distal portion, a combined irrigation and guiding element lumen in the distal portion, and side by side irrigation and guiding element lumens in the proximal portion.

In another embodiment of the device, the guiding element is selected from the group consisting of a sinus illumination system and a guide wire.

In another aspect, the invention is a method for treating a target space in the nasal anatomy. The method includes inserting a medical device into the sinus anatomy, the medical device having a handle, a guiding element, a sinus guide catheter, a balloon dilation catheter having irrigation apertures, a balloon catheter movement mechanism and a guiding element movement mechanism. The method further includes positioning the sinus guide catheter in the nasal anatomy, advancing the guiding element into the target space of the nasal anatomy, advancing the balloon dilation catheter over the guiding element into the target space of the nasal anatomy, inflating the balloon to dilate a target space in the nasal anatomy, deflating the balloon, sliding the guiding element movement mechanism proximally to remove the guiding element from the target space in the nasal anatomy, and irrigating the nasal anatomy through the balloon dilation catheter irrigation apertures.

In another embodiment of the method, the target space in the nasal anatomy is selected from the group consisting of a frontal sinus opening, a maxillary sinus opening, an ethmoid sinus opening and a sphenoid sinus opening.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements.

BRIEF DESCRIPTION OF THE DRAWINGS

FIG. 8 shows a collection of sinus guide catheters with angles useful for positioning of the balloon dilation catheters of the invention.

FIG. 24A is a side view of an alternative embodiment of the balloon dilation catheter according to the invention. FIG.

24B, FIG. 24C, FIG. 24D, FIG. 24E, FIG. 24F and FIG. 24G are cross-sectional views of the catheter of FIG. 24A at different locations along the length of the catheter.

FIG. 25A and FIG. 25B are cross-sectional views of balloon dilation catheters according to another embodiment of the invention.

DETAILED DESCRIPTION

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

Medical devices according to embodiments of the present invention are beneficial in that, for example, their configuration provides for a particularly efficient preparation and treatment of a patient's sinus opening and is mechanically simple. Moreover, the simplicity of the medical devices provides for them to be manufactured in a cost effective manner. In addition, the medical device according to embodiments of the present invention is sufficiently stiff that it can be beneficially employed to access sinus anatomy followed by a convenient remodeling and irrigation of the sinus.

Figure 1:
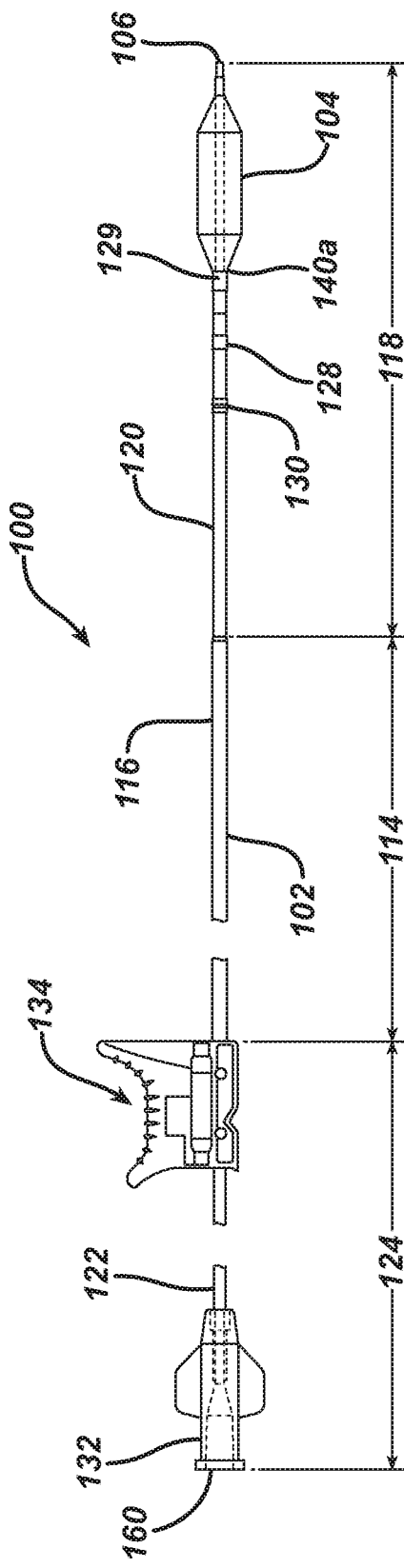
FIG. 1 is a side view of a balloon dilation catheter according to an embodiment of the present invention.

FIG. 1 is a simplified side view of a balloon dilation catheter 100 for the treatment of a target site in the nasal anatomy (for example a frontal sinus opening, maxillary sinus opening, ethmoid sinus opening or sphenoid sinus opening) according to an embodiment of the present invention. Although described with regard to the sinus opening, the inventions described herein may also be useful for the dilation of the Eustachian tube, repair of endo-cranial fractures, airway procedures such as subglottic stenosis dilation and other procedures of the ear, nose and throat. The balloon dilation catheter 100 is a sinus remodeling catheter with an integrated shaft system 102 and a high pressure balloon 104 near the tip 106. The shaft system 102 contains adjacent dual lumen tubing, as will be described in detail below. By adjacent dual lumen tubing is intended that the lumens are next to each other but are spaced apart, one from the other. The construction of the shaft system 102 of the current invention allows for the insertion and retraction of the balloon 104 through the sinus anatomy and the guide catheter lumen (see, e.g. FIGS. 8 and 9, further described herein).

The inflation lumen 108 is used for inflation of the balloon with water, contrast medium or saline through inflation port 160, and the guiding element lumen 110 permits passage of a guidewire or sinus illumination system to facilitate advancement of the balloon dilation catheter 100 to the target site. The balloon dilation catheter 100 is intended to dilate sinus ostia and spaces within the paranasal sinus cavities.

The sinus balloon 104 is designed to be non-compliant or semi-compliant. The diameter of the non-compliant balloon is less sensitive to changes with inflation pressure and that of the semi-compliant balloon will vary somewhat with inflation pressure, and in some instances it will "hourglass" or "dog-bone" about a target region. The balloon itself may be any shape such as triangular, oval or round. In the embodiment shown in FIG. 1, the balloon is round and semi-compliant (nylon) but it may also be made of materials including but not limited to PET, Pebax or multi-layer nylon/Pebax. A hypotube 116 is incorporated on the middle section 114 to provide rigidity during insertion through a sinus guide catheter, as further described below.

The balloon dilation catheter 100 comprises shaft system 102 having a proximal section 124, a middle section 114 and a distal section 118. The balloon dilation catheter distal section 118 comprises a balloon 104 optionally having a soft, atraumatic tip 106 and direct visualization markers 128, 129 and 130. The distal shaft portion 120 of distal section 118 is a flexible shaft material that may be selected from Nylon or pebax or various durometers (including but not limited to 72D, 70D and 63D) or Hytrel having a length of between about 40 mm and 150 mm, often about 60 mm. The shaft diameter is between about 1 and 3 mm, often about 2 mm.

Figure 4:
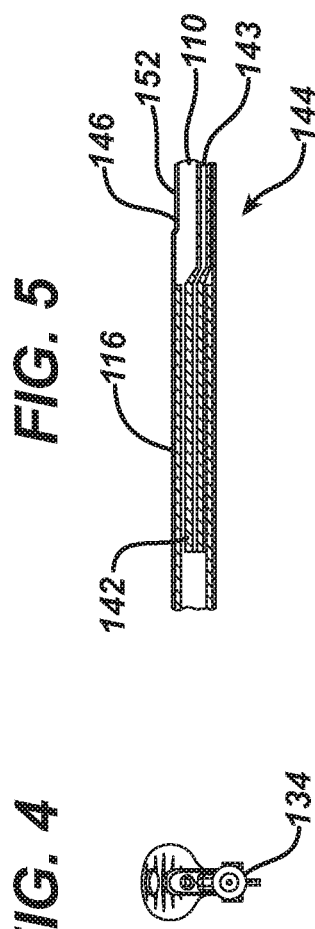
FIG. 4 is an end view of the balloon catheter movement mechanism of the catheter FIG. 1.

The balloon dilation catheter proximal section 124 comprises a luer connector 132 that has an inflation port 160, a balloon catheter movement mechanism 134 (see also FIG. 4) and inflation tubing 122. The inflation tubing 122 is a flexible material selected from Nylon or pebax of various durometers (including but not limited to 72D, 70D and 63D) or Hytrel. The luer connector 132 is bonded to the roughened or unroughened inflation tubing 122, such that the luer connector 132 can be attached to an inflation device (not shown), and can be flexibly moved away from the balloon dilation catheter 100 during a medical procedure. The proximal section 124 has a length of between about 100 mm to 400 mm, often about 320 mm.

Figure 3:
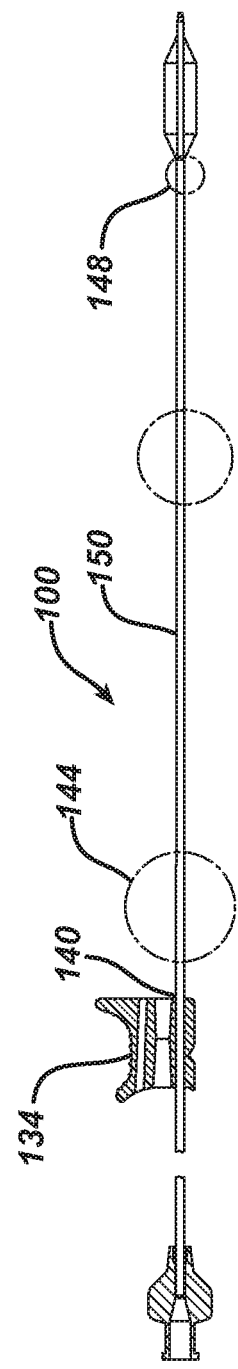
FIG. 3 is a sectional view of the catheter of FIG. 1
Figure 5:
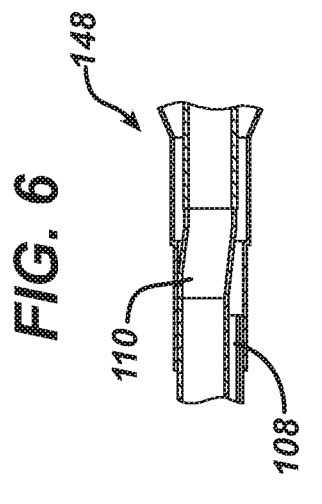
FIG. 5 is an enlarged cut-away view of the mid-inflation tube to proximal inflation tube transition of the catheter of FIG. 1.
Figure 7B:
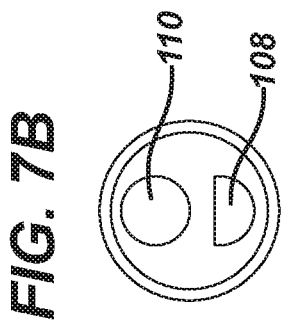
FIG. 7B is a cross-section of the dual lumen and hypotube section of FIG. 7A.
Figure 7A:
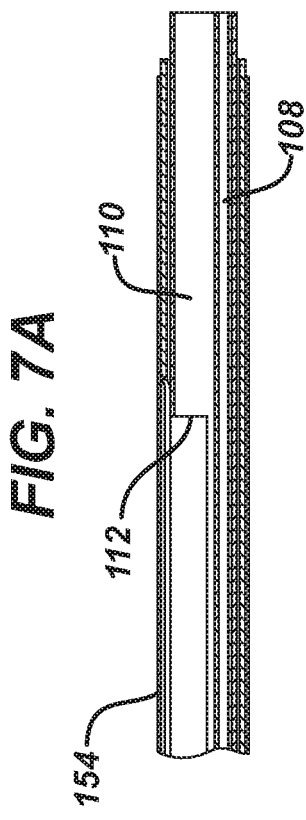
FIG. 7A is an enlarged cut-away view of the dual lumen and hypotube of the catheter of FIG. 1

The middle section 114 of the shaft system 102 is shown in greater detail in FIGS. 3 and 5. The proximal end 140 of the middle section 114 has single lumen inflation tubing that is surrounded by a hypotube 116. Distal to the single lumen inflation tubing is a mid-catheter portion 144 (shown as Circle AB in FIG. 3 and in detail in FIG. 5). Mid-catheter portion 144 comprises a first single lumen inflation tubing section 142, a second single lumen inflation tubing section 143 and the hypotube 116, but also includes a cut-out portion 146 of the hypotube 116 and a polymer jacket 150 (see FIG. 3) over the hypotube 116. The cut-out portion 146 of the hypotube 116 shown in FIG. 5 is in line with the balloon catheter movement mechanism 134 shown in FIG. 3 and guiding element movement mechanism 608 shown in FIG. 9. In an alternative embodiment, the cut-out portion 146 of the hypotube 116 may be rotated with respect to both the balloon catheter movement mechanism 134 and/or the guiding element movement mechanism 608. The inflation lumen 108 may be located 180° apart from the cut-out portion 146 of the hypotube 116, or it may be located between 90° and 180° apart from the cut-out portion 146 of the hypotube 116. The polymer jacket 150 may be constructed of any suitable polymeric material, but is often constructed of relatively stiff and lubricious material such as PEEK (polyetheretherketone). A cut-out section 152 of the polymeric jacket 150 is aligned with the proximal section of the hypotube 116 and a slit section 154 of the polymer jacket 150 is aligned with the distal section of the hypotube 116 (See FIGS. 3 and 7A). Although shown as a polymer jacket 150 with a cut-out section 152 and fixed to the hypotube 116, the polymer jacket 150 may be a complete cylinder (with a small window for initial guiding element entry) fixed to the guiding element movement mechanism 608. In this case, the polymer jacket 150 would slide along with the guiding element movement mechanism 608 and would cover the cut-out portion 146 of the hypotube 116. Alternative embodiments contemplate the use of a metallic material for the polymer jacket, or for spring loading it such that it need not be affixed to the guiding element movement mechanism 608 or for using a loosely wound spring coil around the cut-out portion 146 of the hypotube 116 that is compressed as the guiding element movement mechanism 608 is moved distally down the handle 614.

Figure 6:
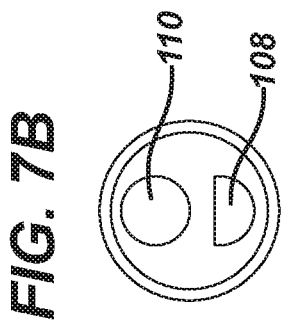
FIG. 6 is an enlarged cut-away view of the dual lumen to balloon transition of the catheter of FIG. 1.

The middle section 114 of the balloon dilation catheter 100 includes a guiding element insertion port 112 (see FIG. 7A) where the guiding element lumen 110 begins. The guiding element lumen 110 and the inflation lumen 108 are side by side lumens (see Circle AC of FIG. 3 and in detail in FIGS. 7A and 7B) that extend from the distal end of the cut-out portion 146 of the hypotube 116 to the balloon transition section 148 shown as Circle AD in FIG. 3 and in detail in FIG. 6). Both the material of the middle section 114 and its dual lumen construction ensure its kink resistance during insertion and retraction of the balloon dilation catheter 100. The middle section 114 has a length of between about 70 mm and 110 mm, often about 90 mm. The shaft diameter is between about 1 and 3 mm, often about 2 mm. The overall length of the balloon dilation catheter 100 is between about 210 mm to about 610 mm, often about 540 mm.

As shown in FIG. 1 in some embodiments, direct visualization markers and/or radiographic markers may be disposed along the integrated shaft system 102. Generally, "direct visualization markers" refers to markers that may be viewed during use with the naked eye or by use of an endoscope, while radiographic markers include radiopaque material and are viewed using a radiographic device such as intra-operative fluoroscopy.

Figure 2:
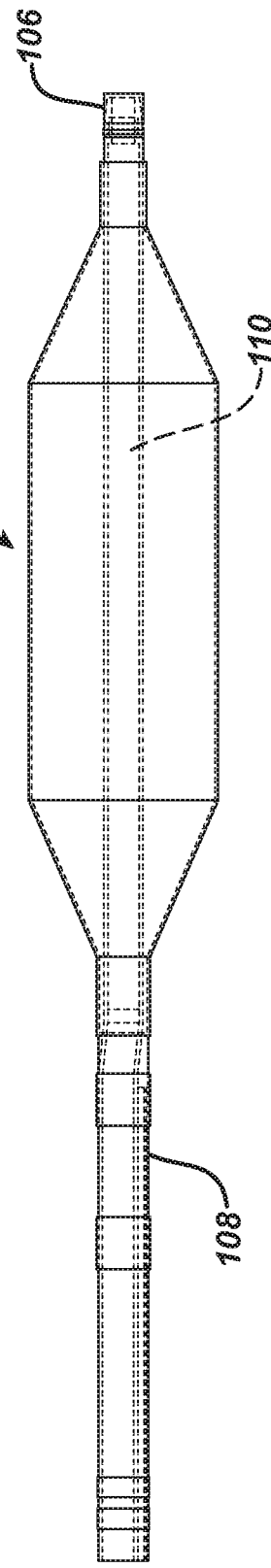
FIG. 2 is an enlarged view of the distal end of the catheter shown in FIG. 1.

Direct visualization markers can be positioned in a number of locations along the integrated shaft system 102. Although one embodiment is described here with reference to FIGS. 1 and 2, other variations may be substituted in alternative embodiments. In one embodiment, shaft system 102 may have a dark color, such as black, dark blue, dark grey or the like, and markers may have a light color, such as white, green, red or the like. In some embodiments, markers may have different colors and/or different widths to facilitate distinguishing the markers from one another during use. This contrast in colors may facilitate viewing the markers in a darkened operation room and/or when using an endoscope inside a patient in the presence of blood.

In one embodiment, there may be a first distal shaft marker 128 (or "endoscopic marker," since it is typically viewed during use via an endoscope) disposed on the distal shaft portion 118 on the shaft system 102 such that the distal edge of the marker is 1 cm.±.0.2 cm from the location where the proximal taper 140a of the balloon 104 meets the shaft system 102. This marker indicates to the user that the shaft location is 1 cm away from the end of the balloon indicating that the balloon has extended from the guide during the procedure.

A second distal shaft marker 130 may be disposed on the shaft system 102 such that the distal edge of the marker is 1 cm.±.0.1 cm from the distal edge of the first distal shaft marker 128. As shown in FIG. 1, the second distal shaft marker is a double marker to distinguish the first and second distal shaft markers 128 and 130 one from one another. The second distal shaft marker 130 indicates the shaft location being 2 cm away from the proximal end of the balloon 104, thus indicating the distance the balloon has extended from the guide during the procedure. In one embodiment, the two markers forming the second distal shaft marker 130 are each 0.75 mm wide and white in color, however, the size and color of the marker can be changed in alternative embodiments. The differences in the first and second distal shaft markers' color, length and number of marks give the indication of the relative location proximal to the balloon under endoscopic visibility. A third distal shaft marker 129 is disposed adjacent the proximal taper 140a the balloon 104. Using an endoscope, the physician user can identify the length of catheter that has been advanced and retracted out of a guide catheter and/or can approximate a location of the balloon 104 relative to patient anatomy such as a paranasal sinus ostium, other paranasal sinus opening, or other openings in the ear, nose or throat. This approximation of balloon position may be very useful in circumstances when the balloon 104 has been advanced far enough into an anatomical location that the balloon 104 can no longer be viewed via endoscope. For example, using the three endoscopic markers, the user is able to endoscopically gauge the distance the catheter has advanced into the frontal recess once the proximal portion of the balloon is no longer visible. Of course, in alternative embodiments, distal shaft markers having different numbers, sizes, colors and positions along the catheter shaft may be used.

FIG. 8 shows a series of sinus guide catheters 200a-200f that may be used in conjunction with the medical device 100. These guide catheters 200a-200f are have a substantially rigid proximal section, a less rigid distal and an atraumatic tip, and each has a preset distal curve of approximately 0 degrees (200a), 30 degrees (200b), 90 degrees (200d), 70 degrees (200c) or 110 degrees (200e and 200f). The guides may have different diameters in the less rigid distal section such as shown in with regard to guide catheter 200e and 200f. Different curvatures are useable to access the ostia of different sinuses. For example, a 70 degree guide is typically used to access the ostium of a frontal sinus, a 90 or 110 degree guide is typically used to access the ostium of a maxillary sinus, etc. Each of these guide catheters 200a-200f has an axial length of about 12.7 cm. These sinus guide catheters are described in U.S. patent application Ser. No. 10/944,270, published as U.S. Pub. No. 2006/0004323 on Jan. 5, 2006, now abandoned and 11/355,512, issued as U.S. Pat. No. 8,894,614 on Nov. 25, 2014 and U.S. Pat. Nos. 7,654,997 and 7,803,150 which are hereby incorporated by reference, and are commercially available as Relieve™ sinus guide catheters from Acclarent, Inc., Menlo Park, Calif.

In the following description, the sinus guide catheter will be referred to as 200a, but any of the guide catheters 200b-f shown in FIG. 8 may be used. Following insertion of the balloon dilation catheter 100 into the sinus guide catheter 200a, a guiding element such as a sinus guidewire (i.e. Relieva Vigor® Sinus Guidewire manufactured by Acclarent Inc, Menlo Park, Calif. and shown in FIG. 6) or sinus illumination system (i.e. Relieva Luma Sentry™ Sinus Illumination System shown manufactured by Acclarent Inc, Menlo Park, Calif.) is inserted through the cut-out potion 146 of the balloon dilation catheter 100 and to the distal tip of the sinus guide catheter 200a. Sinus access is achieved by positioning the sinus guide catheter 200a in the nasal anatomy, and advancing the sinus guidewire or sinus illumination system into the target sinus. Once sinus access has been achieved, the balloon dilation catheter 100 is advanced over the sinus guidewire or sinus illumination system and into the target space. The endoscopic markers on the balloon catheter can be used to assist with placement. The balloon dilation catheter 100 is then inflated to dilate the sinus ostia. Following dilation, the balloon is deflated. The guidewire or sinus illumination system is removed from the nasal anatomy followed by removal of the balloon dilation catheter 100 and sinus guide catheter 200a. The balloon dilation catheter 100 can be prepared for additional sinus dilations in the same patient.

Figure 9:
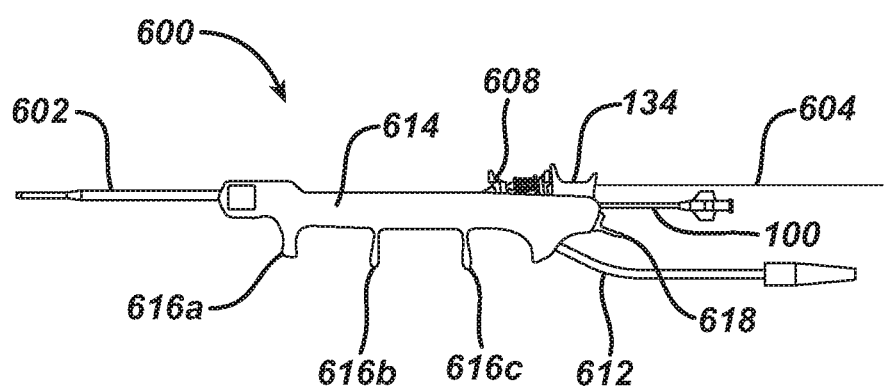
FIG. 9 is a side view of a medical device for the treatment of a sinus opening according to an embodiment of the present invention.

FIG. 9 shows an alternate device with which the balloon catheter of the current invention may be used. This device is described in detail in US Patent Publication No. 2012/0071856, issued as U.S. Pat. No. 9,554,817 on Jan. 31, 2017, which is incorporated by reference herein in its entirety. The medical device 600 includes a guide catheter 602, a guide wire 604, the balloon catheter 100 described herein with an attached balloon catheter movement mechanism 134, a guidewire movement mechanism 608 and a suction pathway 612. The balloon catheter movement mechanism 134 is configured for advancement and retraction of the balloon catheter 100 through the handle 614 and guide catheter 602 by user operation of the balloon catheter movement mechanism 134 using a thumb or single finger. The handle 614 is ergonomically designed such that the finger anchoring pegs 616a, 616b, and 616c can be placed between the fingers of either a right handed or left handed user to provide for support of the device 600. The locking tab 618 prevents the balloon catheter mechanism 134 from moving proximally when it is in the up position, but allows for movement distally. When the locking tab 618 is in the down position, the balloon catheter 100 and guidewire 604 can be inserted into the handle through the guide catheter 602.

The balloon dilation catheter 100 sizes may be 5 mm×16 mm, 6 mm×16 mm and 7 mm×16 mm, or they may be 3.5 mm×12 mm, 6 mm×16 mm or 7 mm×24 mm, although others are within the scope of the invention, including, but not limited to 5 mm×16 mm, 5 mm×24 mm or 7 mm×16 mm. The balloon inflated diameters for the medical devices are as follows: 3.5 mm for the 3.5 mm×12 mm, 5 mm for the 5 mm×16 mm and the 5 mm×24 mm, 6 mm for the 6 mm×16 mm and 6 mm×24 mm, and 7 mm for the 7 mm×24 mm. The balloon inflated working lengths for the medical devices are as follows: 12 mm for the 3.5 mm×12 mm, 16 mm for the 5 mm×16 mm, 6 mm×16 mm and 7 mm×16 mm and 24 mm for the 5 mm×24 mm, 6 mm×24 mm and 7 mm×24 mm. The deflation time of the balloon catheter is about 30 seconds.

The balloon 104 is made of any suitable material know in the art for inflation balloons and may be constructed or semi-compliant of non-compliant materials such as nylon (semi-compliant) and polyethylene terepththalate (PET) (non-compliant). In a particular embodiment, the balloon is constructed of nylon. The atraumatic tip portion 106 is made of a softer material (of lower durometer, i.e. of between about 20D and 55D than the remainder of the balloon catheter and may be made of nylon, pebax or a compound mixture of these materials. Alternatively, the atraumatic tip may be constructed of smaller diameter material (less than about 2.0 mm in diameter, often less than about 1.5 mm in diameter) to ensure it is soft and atraumatic. The tip is approximately 1 mm in length and may contain a 0.5% to 5% colorant for visual or endoscopic visualization and 20% barium sulfate as a radiopaque marker for fluoroscopic visualization in the patient anatomy. The hypotube shaft 116 may be constructed of materials including but not limited to stainless steel and nitinol, and is often is constructed of 304 stainless steel. The combination of materials and catheter construction (the nylon balloon, the soft, atraumatic tip 106 and the adjacent dual lumen design) provides for ease of insertion of the balloon dilation catheter 100 into and removal from the guide catheter 200a or the medical device 600 and navigation through the tortuous sinus anatomy.

Turning now to a further embodiment of the invention, it may be desirable to incorporate devices for irrigation of the sinuses, useful either before or after balloon dilation.

Figure 26:
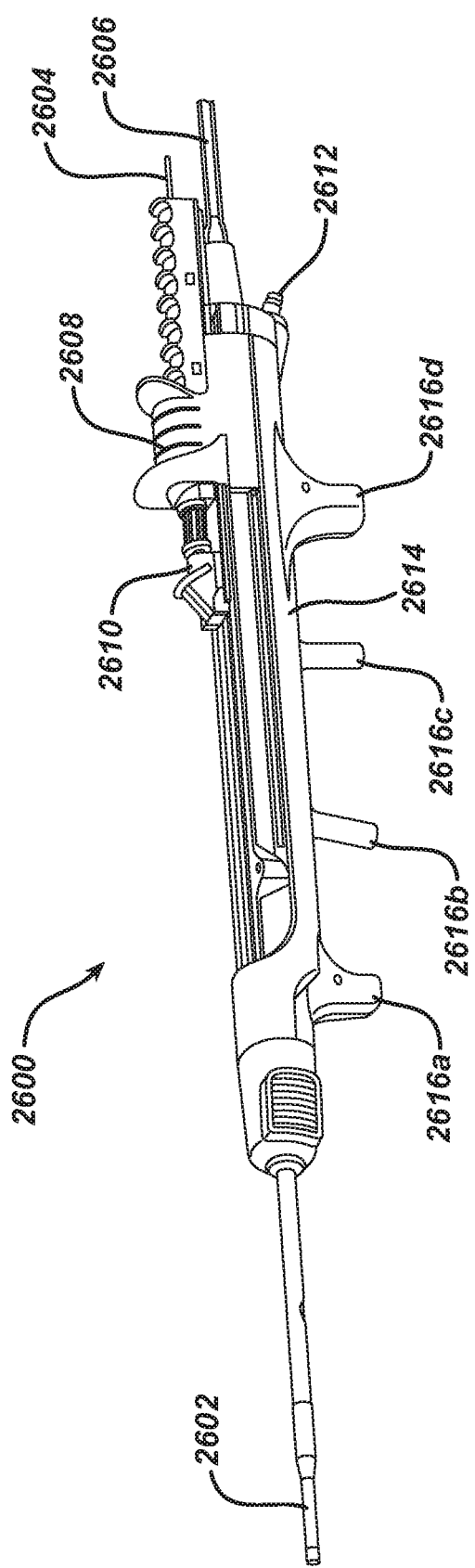
FIG. 26 is a perspective view of a medical device for the treatment and irrigation of a sinus opening according to an embodiment of the present invention

FIG. 26 shows a medical device 2600 according to the invention that includes a guide catheter 2602, a guiding element 2604, in this case an illuminating guidewire, a balloon catheter 2606 with an attached balloon catheter movement mechanism 2608, and a guiding element movement mechanism 2610, and a suction pathway 2612. The guiding element movement mechanism 2610 is configured for advancement, retraction and rotation of the guiding element 2604 and the balloon catheter movement mechanism 2608 is configured for advancement and retraction of the balloon catheter 2606 using a thumb or single finger. The handle 2614 is ergonomically designed such that the finger anchoring pegs 2616a, 2616b, 2626c and 2616d can be placed between the fingers of either a right handed or left handed user to provide for support of the device 2600.

Figure 10:
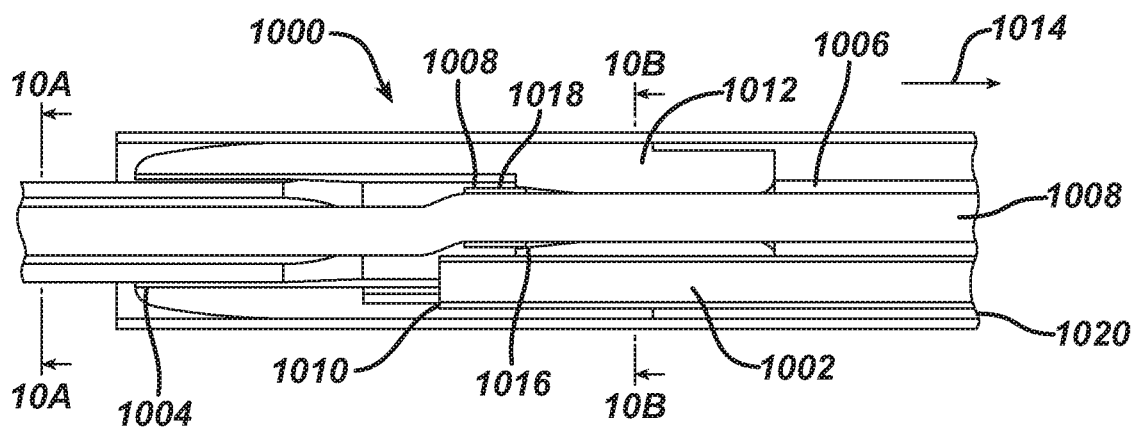
FIG. 10 is an enlarged cut-away view of the integrated shaft system of another embodiment of the present invention
Figure 10A:
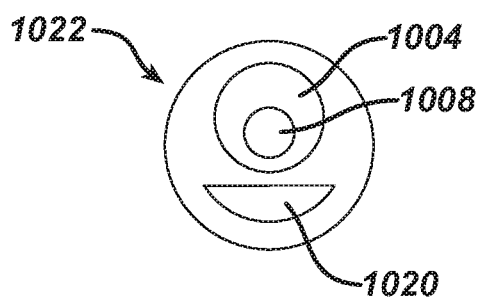
FIG. 10A is a cross section of the distal end of the embodiment shown in FIG. 10
Figure 10B:
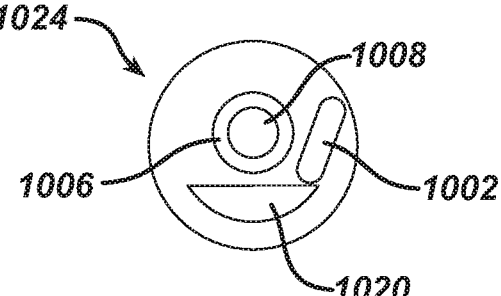
FIG. 10B is a cross-section of the proximal end of the embodiment shown in FIG. 10.

FIG. 10 shows an alternative lumen design and balloon catheter tip configuration for the device shown in FIGS. 3 and 26 such that irrigation of the sinuses can be accomplished either before or after dilation of the sinus ostia using a single-handed system that need not be removed from the sinus in between procedures. In the device shown in FIG. 3, the cut-out portion 146 of the hypotube 116 from the balloon dilation catheter 100 has an altered integrated shaft system 1000 that includes an irrigation lumen 1002 (see FIG. 10). The inflation lumen 1020 extends the length of the integrated shaft system 1000 from the proximal most end to the balloon 104 and provides for inflation of the balloon 104 for dilation of the sinus ostium. As shown in FIG. 10A, the distal portion 1022 of the integrated shaft system 1000 includes a combined lumen 1004 (a combined lumen for irrigation and for containing the guiding element 1008). As shown in FIG. 10B, the proximal portion 1024 of the integrated shaft system 1000 includes a guiding element lumen 1006 and an irrigation lumen 1002 in side by side arrangement. The integrated shaft system 1000 provides for the flow of irrigation liquid from an irrigation port (a luer connector) added to the proximal end of balloon catheter 100 to junction 1010 where it enters the combined lumen 1004. The irrigation liquid exits from the balloon catheter through irrigation apertures (see for example irrigation apertures 1530 in FIG. 15 at the distal end of the balloon catheter 1500 distal to the balloon 1516). Returning to FIG. 10, a plug 1012 is incorporated into the guiding element lumen 1006 to seal off the guiding element lumen 1006 such that when the guiding element 1008 is retracted proximally (in the direction of arrow 1014) to the junction 1010 of the distal end 1016 of the irrigation lumen 1002 and the proximal end of the combined lumen 1004, the guiding element lumen 1006 will be sealed between the stopper 1018 that is attached to the guiding element 1008 (in this case a ring of solder, a thin hypotube or an over-lamination of plastic) and the plug 1012. The irrigation fluid will flow to the balloon distal end rather than out of the cut-out portion 146 of the hypotube 116. In an alternative embodiment, rather than a plug 1012, the guiding element seal area of the guiding element lumen 1006 may be dimensioned to be close to the outer diameter of the guiding element 1008, such that any flow of irrigation fluid through the cut-out portion 145 of the hypotube 116 would be minimal (less than 10%), and the majority (90% or greater) would flow to the balloon distal end.

Figure 11:
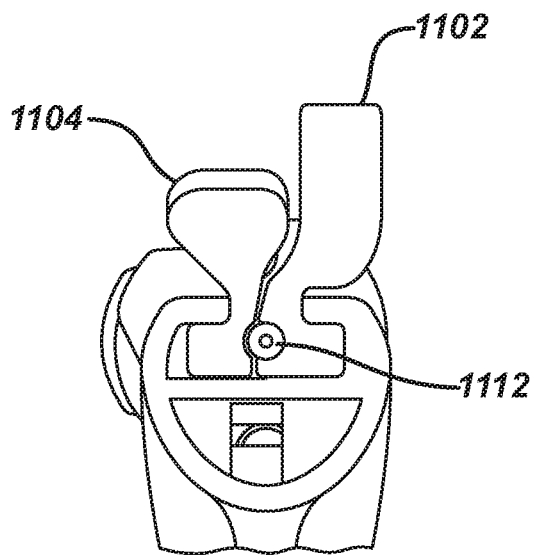
FIG. 11 is an enlarged view of the proximal side of the guiding element movement mechanism and the balloon catheter movement mechanism according to one embodiment of the current invention.
Figure 12:
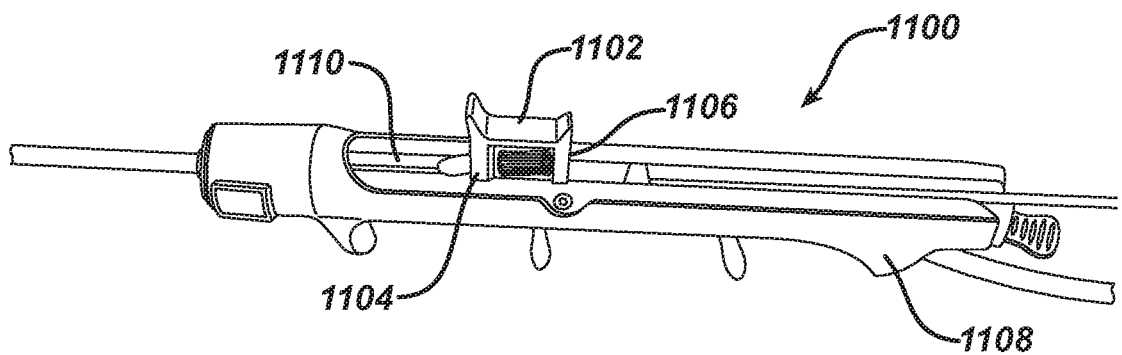
FIG. 12 is a top view of the medical device of a particular embodiment of the invention including the mechanisms of FIG. 11.
Figure 13:
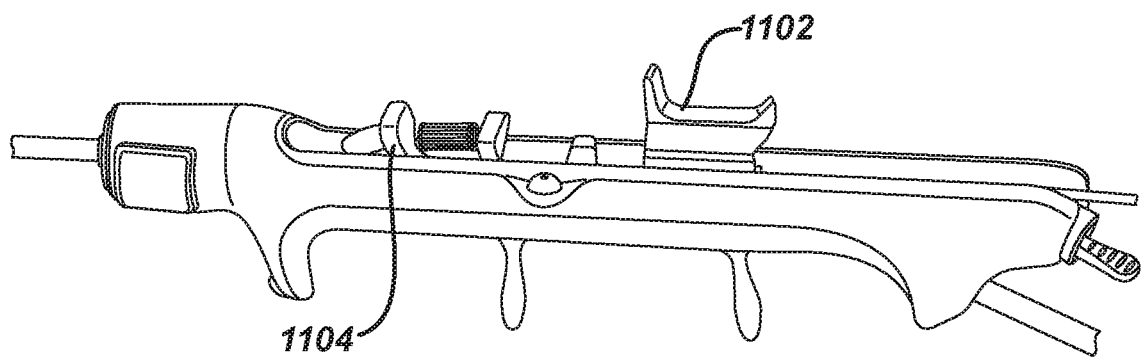
FIG. 13 and FIG. 14 are side views of the medical devices of FIG. 12 with the guiding element movement mechanism in front of the balloon catheter movement mechanism (FIG. 13) and with the balloon catheter movement mechanism in front of the guiding element movement mechanism (FIG. 14).
Figure 14:
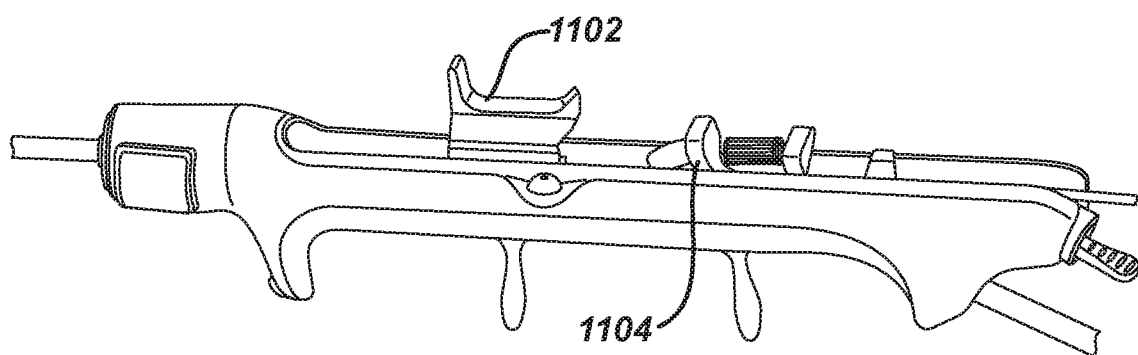

FIG. 11 shows an alternative design for the balloon catheter movement mechanism 134 and the guiding element movement mechanism 608 shown in FIG. 9 in order to accommodate the irrigation lumen described above with regard to FIG. 10. In this design, the balloon catheter movement mechanism 1102 and the guiding element movement mechanism 1104 are not co-linear, that is, they are not shown one behind the other but rather are shown next to each other (although they could be one on top of the other) to allow for proximal movement of the guiding element 1110 out of the irrigation pathway such that irrigation can occur without removal of the device 1100 from the sinus anatomy following treatment (such as balloon dilation) and reinsertion for purposes of irrigation. The balloon catheter movement mechanism 1102 wraps around the balloon shaft 1112, and the mechanisms 1102 and 1104 are shaped and positioned to easily slide past each other without inhibition. FIG. 12 shows the medical device 1100 of the current invention for dilation and irrigation of the sinus ostium. The balloon catheter movement mechanism 1102 and guiding element movement mechanism 1104 are side by side. This configuration occurs when the user is advancing the balloon catheter 100 into the sinus or retracting the guiding element tip 106 into the device 1000. The guiding element movement mechanism 1104 may be connected to the guiding element 1110 by a spring overload mechanism to provide enough force to set the guiding element tip 106 without damaging it. The proximal nub 1106 on the guiding element movement mechanism 1104 allows the user to pull the guiding element movement mechanism 1104 proximally or push it distally when the guiding element movement mechanism 1104 is next to the balloon catheter movement mechanism 110, especially for a user who holds the device 1000 with the guiding element movement mechanism 1104 away from or in the case of a left-handed person, when holding the device 1000 with the guiding element movement mechanism 1104 opposite them. From this configuration, the balloon catheter movement mechanism 1102 can be moved proximally such that it is behind the guiding element movement mechanism 1104 (as shown in FIG. 13). This will occur when the guiding element 1110 is being inserted into the sinus cavity prior to advancement of the balloon 1516 (see FIG. 15) into the ostium. Following dilation and retraction of the balloon 1516, the guiding element 1110 can be retracted such that the guiding element 1110 is removed from the sinus prior to irrigation. The guiding element movement mechanism 1104 would therefore be behind the balloon catheter movement mechanism 1102 as shown in FIG. 14.

Figure 14A:
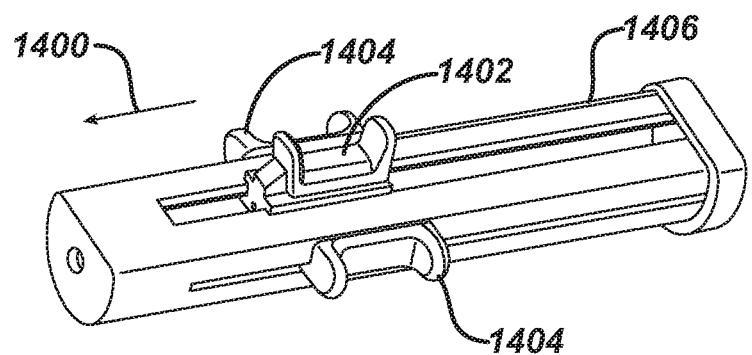
FIGS. 14A, 14B and 14C are alternative embodiments of the guiding element movement mechanism and the balloon catheter movement mechanism of the medical device of FIG. 12.
Figure 14B:
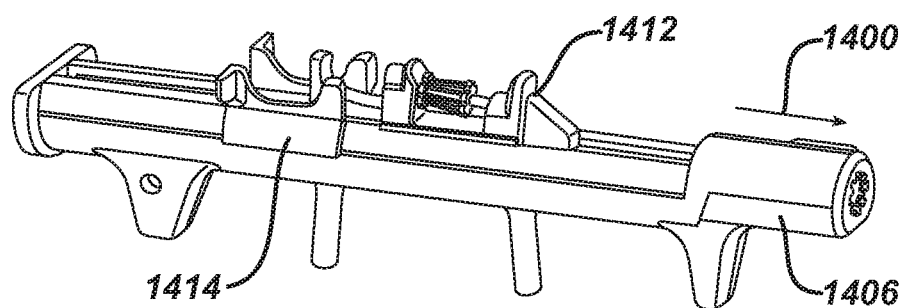
Figure 14C:
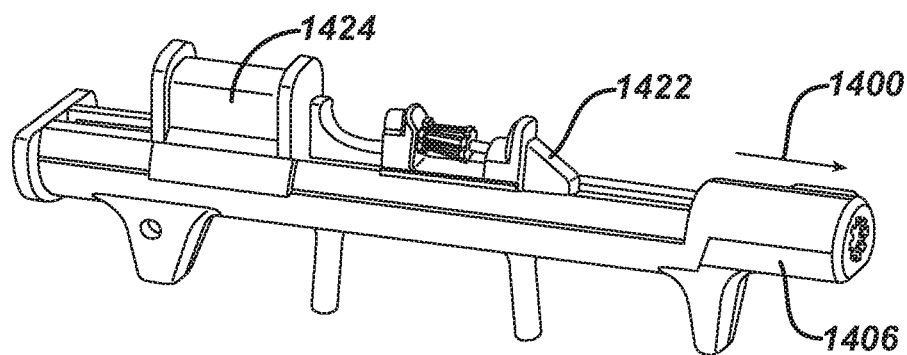

Alternative configurations for locating the balloon catheter movement mechanism 1102 and guiding element movement mechanism 1104 are shown in FIGS. 14A, 14B and 14C. In each of these embodiments, distal movement of the mechanisms is shown by arrow 1400. In FIGS. 14A and 14B the balloon catheter movement mechanisms 1404 and 1414 are located at the side of the handle 1406 and the guiding element movement mechanisms 1402 and 1412 are located on top of the handle 1406. In FIG. 14C the balloon catheter movement mechanism 1424 is located on top of the guiding element movement mechanism 1422. In each of these cases, the mechanisms move independently of each other such that each one can be in front or in back of the other one. The guiding element, therefore, can be inserted into the sinus anatomy and positioned there for access to the sinus cavity (the target space in the nasal anatomy) and during dilation of the ostium and can be retracted there from for irrigation of the sinus cavity through the balloon catheter 1500. In FIGS. 14A, 14B, and 14C, the relative geometry of the user interfacing features may be altered such that the two movement mechanisms may be clearly differentiated from one other tactically (for example by size or by position) and not interfere with one another as they pass by each other. This can allow the user to maintain continuous contact with one or the other movement mechanism as desired. In any of the configurations shown for locating the balloon catheter movement mechanism and guiding element movement mechanism it may be desirable to position and hold in place the two mechanisms with respect to one another or with respect to the handle. Spring-loaded detents, friction elements or magnets may be used to hold the mechanisms in place. Alternatively, a passively activated positive locking latch that would require a different action for release, such as a user operated release button or an automatic release activated by sliding the mechanisms to certain positions within the handle could be employed to lock the mechanisms and thus the balloon 104 and/or the guiding element 604 in place relative to each other and/or the handle 614.

Figure 15:
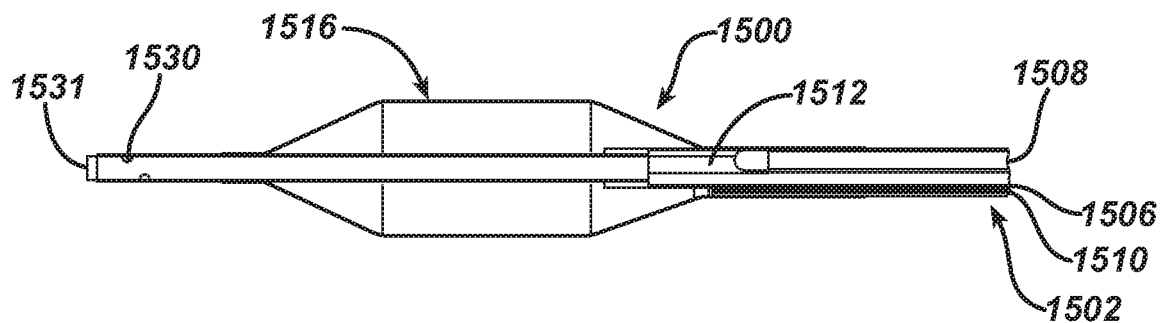
FIG. 15 is an enlarged cut-away view of alternative embodiment of the integrated shaft system of the present invention.
Figure 16:
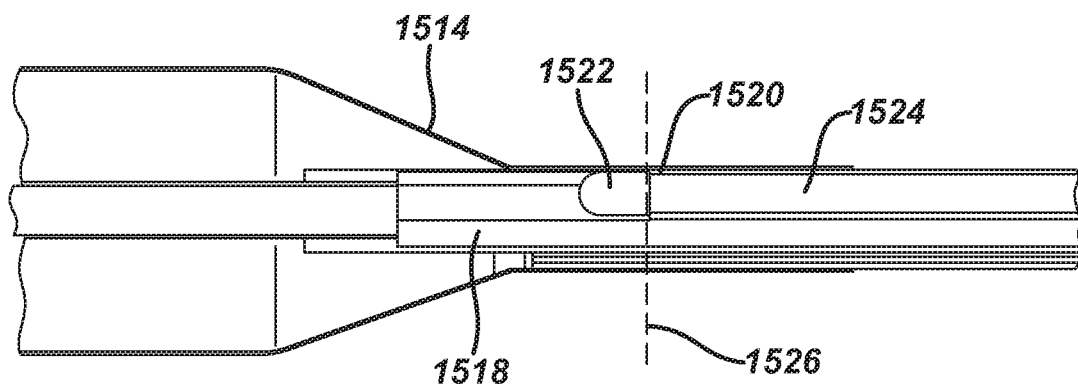
FIG. 16 is further enlarged view of the integrated shaft system shown in FIG. 15.

FIGS. 15 and 16 show a further alternative catheter for dilation and irrigation of the sinus anatomy. In this embodiment, the proximal end 1502 of the integrated shaft system 1504 of the balloon dilation catheter 1500 includes three lumens as shown in FIG. 17A, an irrigation lumen 1506, a guiding element lumen 1508 and an inflation lumen 1510. The lumens are all side by side lumens. In the more distal portion 1512 of the integrated shaft as shown in FIG. 17B, near the proximal taper 1514 of the balloon 1516 of the balloon dilation catheter 1500, the guiding element lumen 1508 and the irrigation lumen 1506 are combined into a combination lumen 1518. The proximal end 1520 of the guiding element tip 1522 of guiding element 1524 is shown located at the juncture 1526 between the combination lumen 1518 and the guiding element lumen 1524 and irrigation lumen 1506. When it is deemed desirable to irrigate the sinus cavity, the guiding element 1524 is retracted proximally to the position shown in FIGS. 15 and 16 such that the proximal end 1520 of the guiding element tip 1522 is seated against the juncture 1526, thereby effectively sealing the guiding element lumen 1508 and preventing flow of irrigation liquid into the guiding element lumen 1508 and out of the cut-out portion 146 of the hypotube 116 shown in FIG. 3, but to allow for flow of irrigation liquid through irrigation apertures 1530 and/or through the proximal end of the balloon dilation catheter 1500 for proper irrigation of the sinuses. The guiding element tip 1522 may be spring loaded to provide the seating force, rather than relying upon the user keeping tension on it.

Referring to FIG. 15, the irrigation apertures 1530 are between about 0.020 inches and about 0.050 inches and there may be any number of apertures between about 1 and 10 apertures, usually between about 2 and 5 apertures, and often 3 apertures. The embodiment shown in FIG. 15 includes a forward facing tip opening 1531 and three radially facing openings 1530, on irrigation tip 106 spaced 120 degrees apart, with the inner diameter of the forward facing tip opening being 0.037 inches and each of the side openings having a inner diameter of 0.026 inches and the inner diameter of the irrigation lumen proximal of the atraumatic tip is about 0.042 inches. Alternative embodiments may include any suitable alternative number of side openings distributed in any suitable pattern such as a helical pattern.

In one embodiment, a first side opening may be placed at about 2.5 mm from the distal end of medical device 100, a second side opening may be placed at about 3.5 mm from the distal end of medical device 100, and a third side opening may be placed at about 4.5 mm from the distal end of medical device 100, with each of these measurements being from the distal end to approximately the center of each side opening. The length of the irrigation tip from the distal end of the medical device 100 to the distal end of the balloon 104 is approximately 7 mm. Each side opening may have any suitable diameter in various alternative embodiments. For example, in one embodiment, each side opening may have a diameter of between about 0.020 inches and about 0.050 inches and or between about 0.030 inches and about 0.040 inches and or about 0.033 inches, so long as the diameter of the irrigation lumen of the irrigation tip proximal of the atraumatic tip 106 is larger than the diameter of the forward facing tip opening.

The length of the balloon dilation catheter distal tip from the distal end of the balloon 1516 to the distal end of the balloon dilation catheter 1500 is between about 5 mm and 10 mm often about 7 mm.

Figure 17:
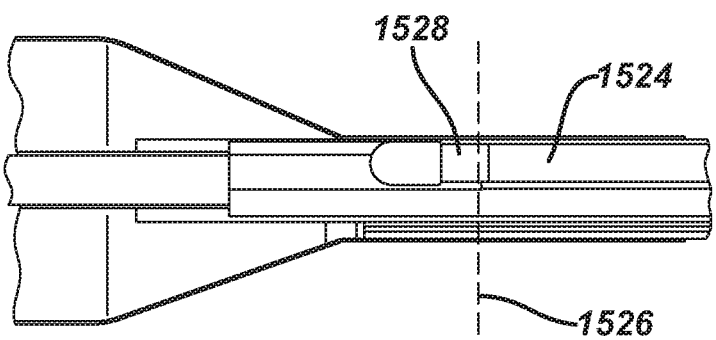
FIG. 17 is an enlarged cut-away view of another embodiment of the integrated shaft system of the present invention.
Figure 17A:
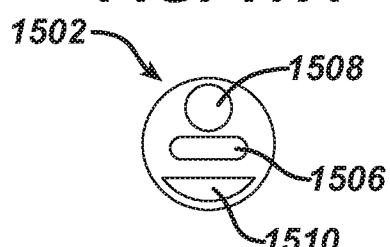
FIG. 17A is a cross section of the proximal end and FIG. 17B is a cross-section of the distal end of the embodiment shown in FIG. 17.
Figure 17B:
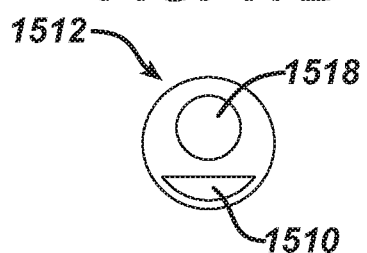

FIG. 17 shows an alternative to the device shown in FIGS. 15 and 16. In addition to the distal tip 1522 of the guiding element 1524, a plug 1528 is included on the guiding element 1524, in this case a hypotube welded onto the coil of the guiding element 1524 to aid in sealing the guiding element lumen 1508 at the juncture 1526 and prevent flow of irrigation liquid into the guiding element lumen 1508 and out of the cut-out portion 146 of the hypotube 116, when the guiding element is retracted during irrigation.

FIGS. 24A, B, C, D, E and F are alternative designs for the balloon catheter assembly 2400 according to the invention. The balloon catheter assembly shown in FIG. 24A has a mid-catheter joint 2402 that is further shown in FIG. 24E. The balloon catheter assembly has an inflation port 2404, an irrigation port 2406 and cut-out portion 2408 for insertion of the guiding element (not shown). As is further shown in FIG. 24A, the assembly 2400 has a proximal section 2410, a middle section 2412 and a distal section 2414. A cross-section of the catheter shaft 2416 in the proximal section 2410 is shown in FIG. 24B. The catheter shaft 2416 includes an irrigation tube 2418, an irrigation lumen 2420, an inflation tube 2422 and an inflation lumen 2424 in co-axial arrangement. A cross-section of the catheter shaft 2416 in the middle section 2412, proximal to the mid-catheter joint 2408 is shown in FIG. 24C. An inflation tube 2426 and an inflation lumen 2428 remain in coaxial arrangement with the irrigation tube 2430 and irrigation lumen 2432. A sleeve 2434 (in this case a hypotube) is in coaxial arrangement with the irrigation tube 2430, but an opening 2436 in the sleeve 2434 allows for insertion of the guiding element (not shown). A cross-section of the catheter shaft 2416 in the distal section 2414 is shown in FIG. 24D. This distal catheter shaft 2438 includes side by side lumens, an inflation lumen 2440 and an irrigation and guiding element lumen 2442.

The mid-catheter joint 2408 is further shown in FIG. 24E. A cross-section of the catheter shaft 2416 in the proximal portion 2450 of the mid-catheter joint 2408 is shown in FIG. 24F and a cross-section of the catheter shaft 2416 in the distal portion 2452 of the mid-catheter joint 2408 is shown in FIG. 24G. As shown in FIG. 24F, a inflation tube 2454 with an inflation lumen 2456 is coaxially within an irrigation tube 2458 with an irrigation lumen 2460. In side by side arrangement is a guiding element lumen 2464. A hypotube 2466 surrounds both the guiding element lumen 2464 and the irrigation tube 2458. Between the hypotube 2466 and the guiding element lumen 2464 and the irrigation tube 2458 is the coupler 2470. The coupler 2470 is a tube that bridges across the mid-catheter joint 2408 from its distal end 2452 to its proximal end 2450. As shown in FIG. 24G, the coupler 2470 surrounds the inflation lumen 2472 and the guiding element lumen 2464 and irrigation lumen 2474 which are in side by side arrangement. The transition section 2480 between the proximal portion 2450 and distal portion 2452 provides for the combination of the guiding element lumen 2464 and the irrigation lumen 2460 of the proximal portion 2450 into the combination of the guiding element and irrigation lumen 2474 of the distal portion 2452. In a further embodiment of the invention, a liner (often polymeric and often a PTFE liner) may be included inside the combination lumen 2474 such that when the balloon catheter 2400 is placed within an angled guide catheter (such as shown in FIG. 8), the combined irrigation and guiding element tube 2476 will provide lubricity and kink resistance for the advancement, retraction and rotation of the guiding element.

FIGS. 25A and 25B are alternative cross-sectional designs for the proximal portion shown in FIG. 24F of the catheter assembly 2400. In this embodiment, rather than a coaxially arranged inflation and irrigation lumen, the guiding element lumen 2516 and the irrigation lumen 2514 remain separate, side by side lumens and are further in side by side arrangement with the guiding element lumen 2516. The proximal portion shown in FIG. 25A includes an inflation lumen 2502 and an irrigation lumen 2504 in side by side arrangement.

Figure 18A:
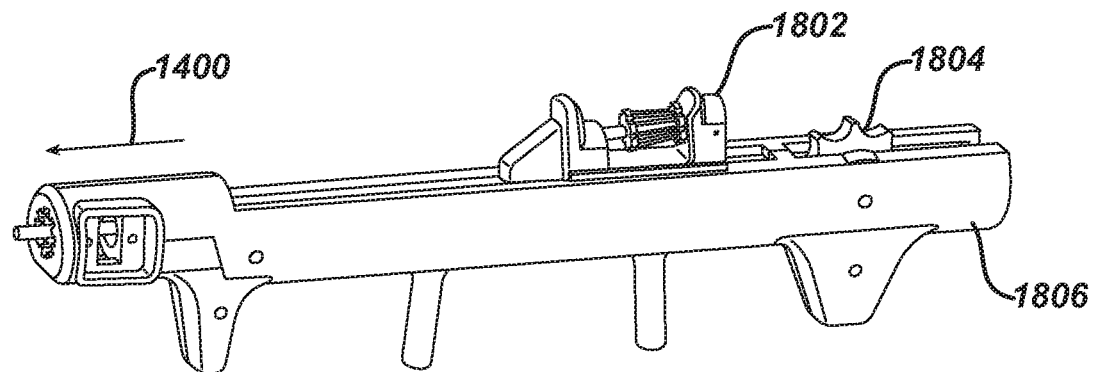
FIG. 18A is a side view of alternative embodiment of the handle of the medical device of the invention.
Figure 18B:
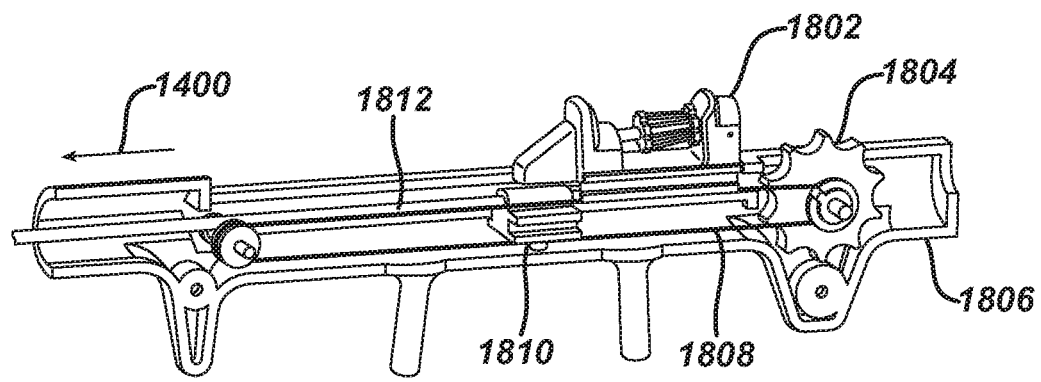
FIG. 18B is a cut-away view of the handle of FIG. 18A.

With reference to FIGS. 11, 12, 13, 14 and 14A, 14B and 14C, further alternative configurations for locating the balloon catheter movement mechanism and guiding element movement mechanism are shown in FIGS. 18A and 18B, 19A and 19B, 20A and 20B, 21A and 21B, 22A, 22B and 22C and 23. In each of these embodiments, distal movement of the mechanisms is shown by arrow 1400. In FIGS. 18A and 18B the balloon catheter movement mechanism 1804 is a rotating thumbwheel that is fixed to the handle 1806. The balloon catheter movement mechanism 1804 drives the balloon catheter through a belt 1808 or counter wrapped string drive attached to a balloon carriage 1810. Alternative methods for driving the balloon include a rack and pinion, other types of gear and shaft systems, a rotating leadscrew type drive or a linear/rotational racheting system with a slider or lever. In the embodiments shown in FIGS. 18A and 18B, the guiding element movement mechanism 1802 is located on top of the handle 1806. The guiding element movement mechanism 1802 (and the guiding element, not shown) slides over the balloon catheter 1812 such that the guiding element and balloon catheter 1812 can be positioned independently. Additionally, there is a clear tactile differentiation between the guiding element movement mechanism 1802 and the balloon catheter movement mechanism 1804 since one is a moving slider and the other is a wheel that rotates in place. An alternate version of the embodiment shown in FIGS. 18A and 18B contemplates a slider for the balloon catheter movement mechanism and a fixed thumbwheel or roller for the guiding element movement mechanism. Alternatively both movement mechanisms could be fixed thumbwheels or rollers.

Figure 19A:
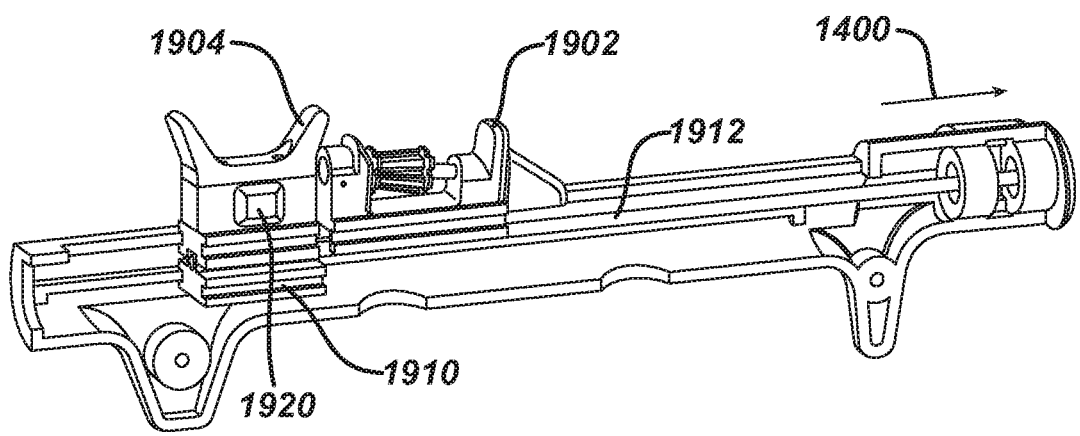
FIG. 19A and FIG. 19B are cut-away views of alternative embodiment of the handle of the medical device of the invention.
Figure 19B:
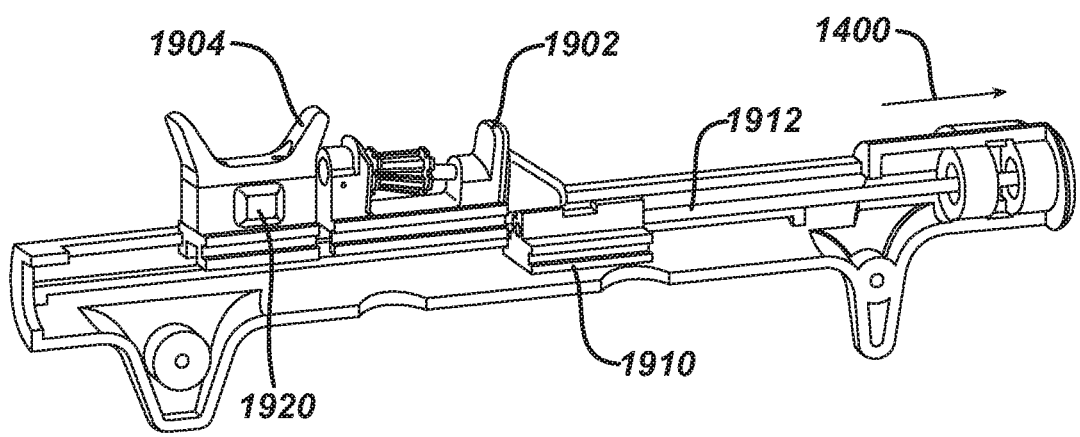

In FIGS. 19A and 19B, the guiding element movement mechanism 1902 and the balloon catheter movement mechanism 1904 appear to the user as two separate slider mechanisms that are coaxial in the same track. However, the balloon catheter movement mechanism 1904 is a coupled to a balloon catheter carriage 1910, the balloon catheter movement mechanism 1904 being separable from the balloon catheter carriage 1910. The balloon catheter balloon carriage 1910 is attached to the balloon catheter 1912. As shown in FIG. 19A, the balloon catheter movement mechanism 1904 is coupled to the balloon catheter carriage 1910 as the balloon catheter 1912 is positioned within the sinus anatomy. Once the balloon catheter carriage 1910 is positioned as shown in FIG. 19B, the balloon catheter movement mechanism 1904 can be decoupled from the balloon carriage 1910 and moved proximally away from the balloon carriage 1910, thus allowing the guiding element movement mechanism 1902 to slide proximally past the balloon catheter carriage 1910 to move the guiding element out of the irrigation pathway as described previously. The de-coupling of the balloon catheter movement mechanism 1904 from the balloon carriage 1910 can be accomplished by the user, for instance by pushing a spring loaded button 1920 such that the balloon catheter movement mechanism 1904 and the balloon carriage 1910 can separate. Alternatively, the user can flip a two-state (bi-stable) toggle or button to an unlocked position such that the balloon catheter movement mechanism 1904 and the balloon carriage 1910 can separate.

Re-coupling of the balloon catheter mechanism to the balloon carriage can be accomplished actively, for example, by the user pushing the button to a different state, or passively, for example where the balloon catheter mechanism automatically reattaches with a spring loaded lock as it slides over the carriage. Alternative designs for this embodiment would include a guiding element movement mechanism that is not attached to the guiding element, but that is attached to a guiding element carriage such that the guiding element movement mechanism and guiding element carriage could be detached one from the other through user activation of a spring loaded button, or a single external mechanism for both the balloon catheter and the guiding element that could engage and couple and decouple with either the guiding element or the balloon catheter through a user activated push button mechanism or other action.

Figure 20A:
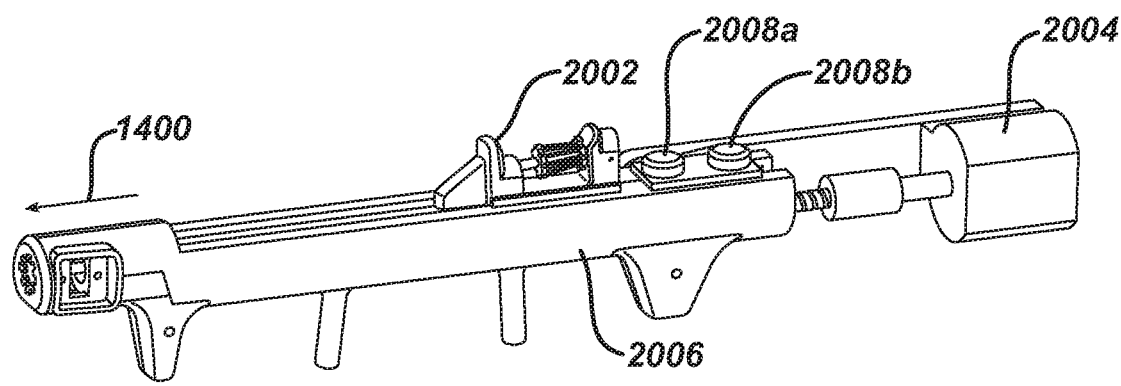
FIG. 20A is a side view of alternative embodiment of the handle of the medical device of the invention.
Figure 20B:
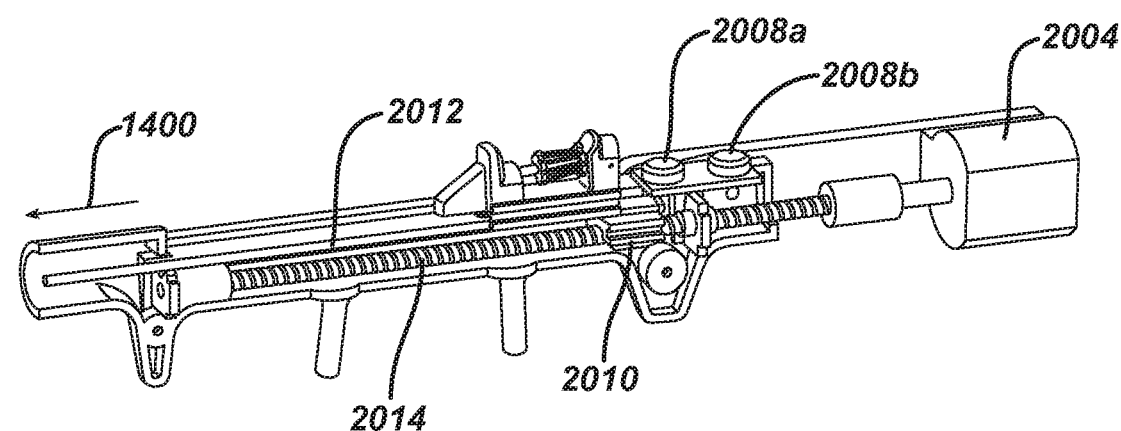
FIG. 20B is a cut-away view of the handle of FIG. 20A.

FIGS. 20A and 20B show the design of a handle 2006 for a medical device 600 where a guiding element movement slider mechanism 2002 is used to move a guiding element but the balloon catheter movement mechanism is replaced with a motor 2004 that is controlled through switches. The switches shown in FIGS. 20A and 20B are push buttons 2008a and 2008b, but could also be rocker type or other switches known in the art. These switches could incorporate variable speed. Since there is no external movable control for the balloon catheter (not shown), the guiding element movement mechanism 2002 can pass freely above and proximal to the balloon carriage 2010. The motor can drive the balloon catheter through a balloon drive leadscrew as shown in FIG. 20B or another arrangement such as a rack and pinion, belt drive or other transmission type known in the art. The motor 2004 may be electrically powered through either a battery or external power source, or may be a pneumatically driven motor running off of a suction pump or hydraulically driven such as an irrigation pump.

Figure 21A:
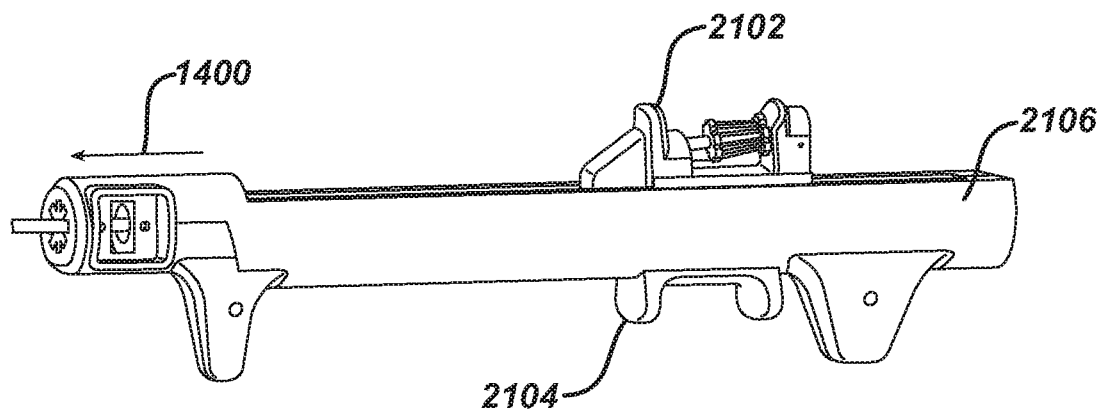
FIG. 21A is a side view of alternative embodiment of the handle of the medical device of the invention.
Figure 21B:
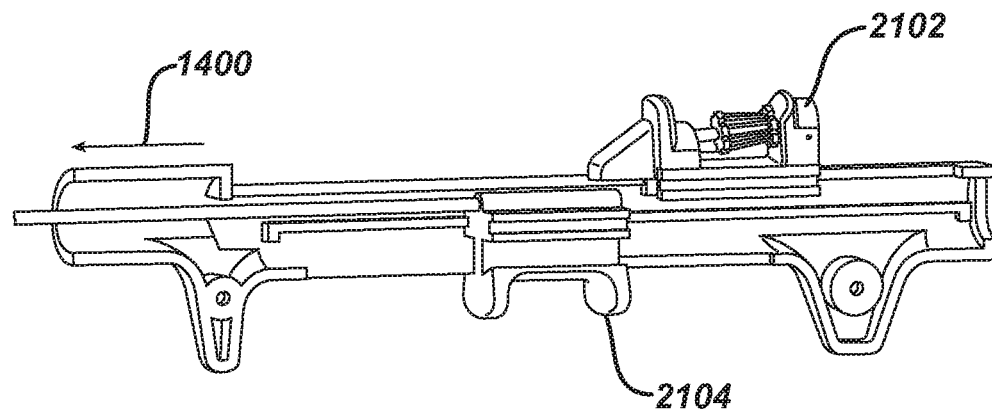
FIG. 21B is a cut-away view of the handle of FIG. 21A.

In FIGS. 21A and 21B the guiding element movement mechanism 2102 is located on top of the handle 2106 and the balloon catheter movement mechanism 2104 is located on the bottom the handle 2106. The location of the guiding element movement mechanism 2102 and the balloon catheter movement mechanism 2104 could be reversed such that the guiding element movement mechanism 2102 is on the bottom and the balloon catheter movement mechanism 2104 is on the top. In either case, the mechanisms move independently of each other such that each one can be in front or in back of the other one. The guiding element, therefore, can be inserted into the sinus anatomy and positioned there for access to the sinus cavity (the target space in the nasal anatomy) and during dilation of the ostium and can be easily retracted therefrom by the use of easily operated handle control for irrigation of the sinus cavity through the balloon catheter without removing the medical device 600 from the surgical field or without requiring addition personnel to aid in retraction of the guiding element.

Figure 22A:
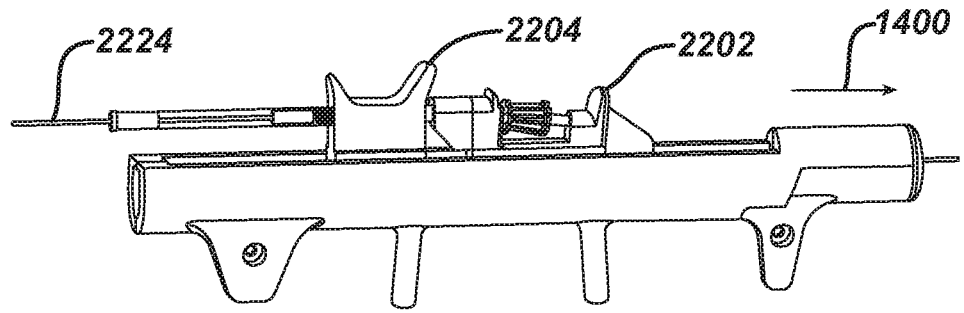
FIG. 22A is a side view of an alternative embodiment of the handle of the medical device of the invention.
Figure 22B:
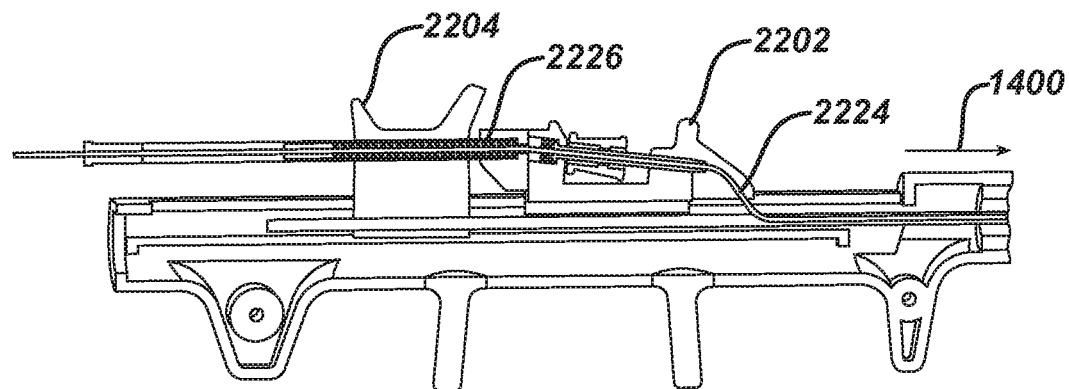
FIG. 22B is a cut-away view of the handle of FIG. 22A when the device is configured for dilation of the sinus ostium.
Figure 22C:
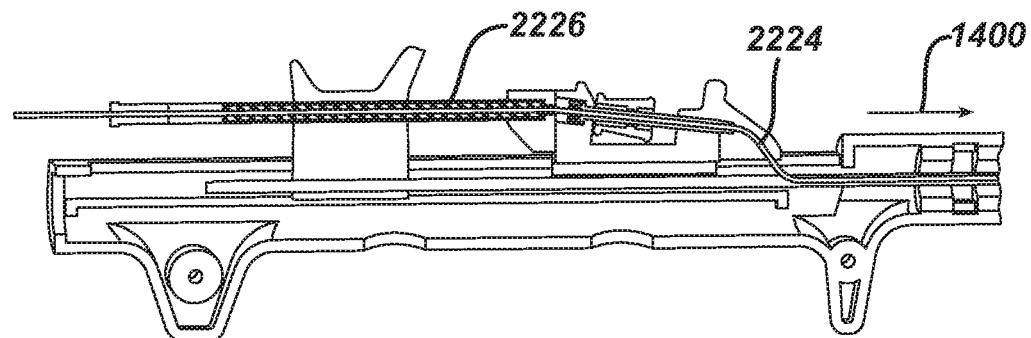
FIG. 22C is a cut-away view of the handle of FIG. 22A when the device is configured for irrigation.

In FIGS. 22A, 22B and 22C, the guiding element movement mechanism 2202 and the balloon catheter movement mechanism 2204 are coaxial in the same track. As shown in FIG. 22B, the guiding element 2224 is holding in a spring 2226 in a compressed state in the guiding element movement mechanism 2202 during positioning of the guiding element 2224 and the balloon catheter (not shown). When irrigation is desired, the guiding element 2224 is released from the guiding element movement mechanism (see FIG. 22C) through a clamp release or button that decompresses the spring 2226. The guiding element 2224 becomes loose in the guiding element movement mechanism 2202 and automatically moves proximally out of the irrigation pathway. After the spring has been deployed (uncompressed), in order to reset the device to non-irrigation mode the guiding element and spring would need to be reset (the spring must be re-compressed). This may be accomplished by pulling on the guiding element in the direction of arrow 1400, a user activated plunger type mechanism to recompress the spring from the proximal side, or a spring reset-mechanism incorporated into the handle or around the guiding element.

Figure 23:
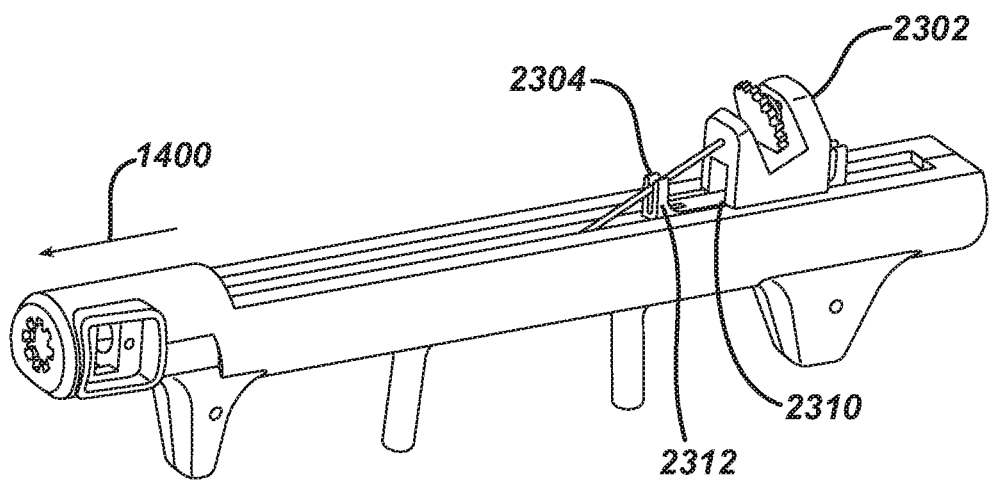
FIG. 23 is a side view of an alternative embodiment of the handle of the medical device of the invention.

In the embodiment shown in FIG. 23, the guiding element movement mechanism 2302 has a tunnel 2310 and the protrusions 2312 of the balloon catheter movement mechanism 2304 are small enough to pass underneath the guiding element movement mechanism 2302. The guiding element movement mechanism 2302 can pass over the balloon catheter movement mechanism 2304 for retraction of the guiding element and consequent use of irrigation. The user can maintain continuous contact with the guiding element movement mechanism 2302 as the guiding element is retracted and movement of the fingers is not required in order for the guiding element movement mechanism 2302 to move distal to the balloon catheter movement mechanism 2304.

It may be desirable to use an endoscope in conjunction with the device 600 or device 1100 of the invention, for visualization of the treated region. It may be desirable to include a feature with the device 600 or the device 1000 to avoid any interference that might occur between the proximal end of the endoscope and the proximal end of the device. A rotational and articulating element such as a ball and socket is inserted between the handle 614 and the guide catheter 602 shown in FIG. 9. The element may be adjustable within a given range of rotation and bend angles or may have discrete position, dictated by the user either prior to or during the method of the invention.

The invention has been described with reference to certain examples or embodiments of the invention, but various additions, deletions, alterations and modifications may be made to those examples and embodiments without departing from the intended spirit and scope of the invention. For example, any element or attribute of one embodiment or example may be incorporated into or used with another embodiment or example, unless otherwise specified or if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. An apparatus comprising:
   (a) a handle having a distal end;
   (b) a guide shaft extending distally from the distal end of the handle;
   (c) a guiding element for accessing a passageway in a head of a patient, the guiding element being slidable relative to the guide shaft;
   (d) a dilation catheter for dilating a passageway in a head of the patient, the dilation catheter being slidable relative to the guide shaft;
   (e) a dilation catheter actuator slidable along the handle; and
   (f) a guiding element actuator slidable along the handle;
   wherein the dilation catheter actuator and the guiding element actuator are slidable along the handle for single handed movement of the guiding element and dilation catheter to access and dilate the passageway in the head of the patient while the guide shaft is disposed in the head of the patient;
   wherein the guiding element actuator and the dilation catheter actuator are configured to be longitudinally co-located with each other;
   wherein the dilation catheter actuator is located on top of the guiding element actuator and is configured to slide over the guiding element actuator.

* * * * *